US012016966B2

(12) United States Patent
Childers et al.

(10) Patent No.: US 12,016,966 B2
(45) Date of Patent: Jun. 25, 2024

(54) STERILIZATION CONTAINER WITH BATTERY POWERED SENSOR MODULE FOR MONITORING THE ENVIRONMENT IN THE CONTAINER

(71) Applicant: Stryker Corporation, Kalamazoo, MI (US)

(72) Inventors: Robert W. Childers, Trinity, FL (US); Bruce Henniges, Galesburg, MI (US)

(73) Assignee: Stryker Corporation, Kalamazoo, MI (US)

(*) Notice: Subject to any disclaimer, the term of this patent is extended or adjusted under 35 U.S.C. 154(b) by 1121 days.

(21) Appl. No.: 16/791,422

(22) Filed: Feb. 14, 2020

(65) Prior Publication Data
US 2020/0179551 A1 Jun. 11, 2020

Related U.S. Application Data

(60) Division of application No. 15/259,213, filed on Sep. 8, 2016, now Pat. No. 10,583,214, which is a
(Continued)

(51) Int. Cl.
*A61L 2/28* (2006.01)
*A61L 2/07* (2006.01)
(Continued)

(52) U.S. Cl.
CPC ........ *A61L 2/28* (2013.01); *A61L 2/07* (2013.01); *G01K 1/026* (2013.01); *G01K 7/22* (2013.01);
(Continued)

(58) Field of Classification Search
CPC .................................. A61L 2/28; G01K 7/22
See application file for complete search history.

(56) References Cited

U.S. PATENT DOCUMENTS 5,167,243 A 12/1992 Cowan et al.
5,565,634 A 10/1996 Graessle et al.
(Continued)

FOREIGN PATENT DOCUMENTS

CN 1151703 A 6/1997
CN 1441888 A 9/2003
(Continued)

OTHER PUBLICATIONS

English language abstract for CN 1151703 A extracted from espacenet.com database on Jun. 3, 2021, 2 pages.
(Continued)

*Primary Examiner* — Donald R Spamer
(74) *Attorney, Agent, or Firm* — McDonnell Boehnen Hulbert & Berghoff LLP

(57) ABSTRACT

A sterilization container with a sensor module for monitoring the environmental characteristics internal to the container. The sensor module includes a normally closed end bore. A sensor is disposed in the closed end void space. Other sensors also part of the module monitor the pressure and temperature of the environment inside the container. Based on the measurements of the environment in the container and the environment within the closed end void space it is possible to determine the extent to which the container is filled with saturated steam.

19 Claims, 20 Drawing Sheets

Related U.S. Application Data continuation of application No. PCT/US2015/019724, filed on Mar. 10, 2015.

(60) Provisional application No. 61/951,178, filed on Mar. 11, 2014.

(51) Int. Cl.

| | | |
|---|---|---|
| *G01K 1/02* | (2021.01) | |
| *G01K 7/22* | (2006.01) | |
| *G01L 9/00* | (2006.01) | |
| *G01L 19/00* | (2006.01) | |
| *G01N 21/33* | (2006.01) | |
| *G01N 21/3504* | (2014.01) | |

(52) U.S. Cl.
CPC ........ *G01L 9/0072* (2013.01); *G01L 19/0092* (2013.01); *G01N 21/33* (2013.01); *G01N 21/3504* (2013.01); *A61L 2202/14* (2013.01); *A61L 2202/24* (2013.01)

(56) References Cited

U.S. PATENT DOCUMENTS

| | | |
|---|---|---|
| 5,788,925 A | 8/1998 | Pai et al. |
| 6,269,680 B1 | 8/2001 | Prieve et al. |
| 6,318,151 B1 | 11/2001 | Wang et al. |
| 6,517,775 B1 | 2/2003 | Wang et al. |
| 6,528,016 B1 | 3/2003 | Kohler et al. |
| 6,532,794 B2 | 3/2003 | Wang et al. |
| 6,537,491 B1 | 3/2003 | Wang et al. |
| 6,612,149 B2 | 9/2003 | Wang et al. |
| 6,875,399 B2 | 4/2005 | McVey |
| 6,930,493 B2 | 8/2005 | Kaiser et al. |
| 7,079,759 B2 | 7/2006 | Tokutake et al. |
| 7,090,808 B2 | 8/2006 | Caputo et al. |
| 7,122,150 B2 | 10/2006 | Gonzalez et al. |
| 7,157,045 B2 | 1/2007 | McVey |
| 7,198,760 B1 | 4/2007 | Wagner |
| 7,827,845 B2 | 11/2010 | Kraus |
| 7,880,887 B2 | 2/2011 | Olson et al. |
| 8,071,021 B2 | 12/2011 | Hill |
| 9,523,614 B2 | 12/2016 | Hermsen et al. |
| 10,022,464 B2 | 7/2018 | Sarphati et al. |
| 10,583,214 B2 | 3/2020 | Childers et al. |
| 2002/0034823 A1* | 3/2002 | Kuepper .................. A61L 2/28 436/1 |
| 2004/0071590 A1 | 4/2004 | Sawyer |
| 2005/0238530 A1 | 10/2005 | Frieze et al. |
| 2006/0088441 A1 | 4/2006 | Hill |
| 2015/0374868 A1 | 12/2015 | Bruce et al. |

FOREIGN PATENT DOCUMENTS

| | | |
|---|---|---|
| CN | 1833729 A | 9/2006 |
| CN | 1977979 A | 6/2007 |
| CN | 101080242 A | 11/2007 |
| CN | 101520424 A | 9/2009 |
| CN | 202342500 U | 7/2012 |
| CN | 103201600 | 5/2015 |
| EP | 0028542 A1 | 5/1981 |
| EP | 1230936 A1 | 8/2002 |
| EP | 1715302 A1 | 10/2006 |
| JP | H11267185 A | 10/1999 |
| JP | H11513285 A | 11/1999 |
| JP | 2002515970 A | 5/2002 |
| JP | 2005514170 A | 5/2005 |
| JP | 2013541369 A | 11/2013 |
| WO | 9719709 A1 | 6/1997 |
| WO | 2012/065109 | 5/2012 |

OTHER PUBLICATIONS

English language abstract for CN 1441888 A extracted from espacenet.com database on Jun. 3, 2021, 2 pages.
English language abstract and machine-assisted English language translation for CN 1833729 A extracted from espacenet.com database on Jun. 3, 2021, 9 pages.
English language abstract for CN 101080242 A extracted from espacenet.com database on Jun. 3, 2021, 1 page.
English language abstract and machine-assisted English language translation for CN 101520424 A extracted from espacenet.com database on Jun. 3, 2021, 9 pages.
English language abstract and machine-assisted English language translation for CN 202342500 U extracted from espacenet.com database on Jun. 3, 2021, 5 pages.
English language abstract and machine-assisted English language translation for EP 1 715 302 A1 extracted from espacenet.com database on Jun. 3, 2021, 9 pages.
International Search Report for Application No. PCT/US2015/019724 dated Aug. 24, 2015, 5 pages.
English language abstract and machine-assisted English Translation for CN 1977979 extracted from espacenet.com database on Jan. 23, 2019, 20 pages.
English language abstract and machine-assisted English language translation for JPH 11-267185 extracted from espacenet.com database on Feb. 8, 2019, 13 pages.
English language abstract for JPH 11-513285 extracted from espacenet.com database on Feb. 8, 2019, 1 page.
English language abstract for JP 2013-541369 extracted from espacenet.com database on Feb. 8, 2019, 1 page.
English language abstract for JP 2002-515970 extracted from espacenet.com database on Jun. 1, 2020, 1 page.
English language abstract for JP 2005-514170 extracted from espacenet.com database on Jun. 1, 2020, 1 page.

* cited by examiner

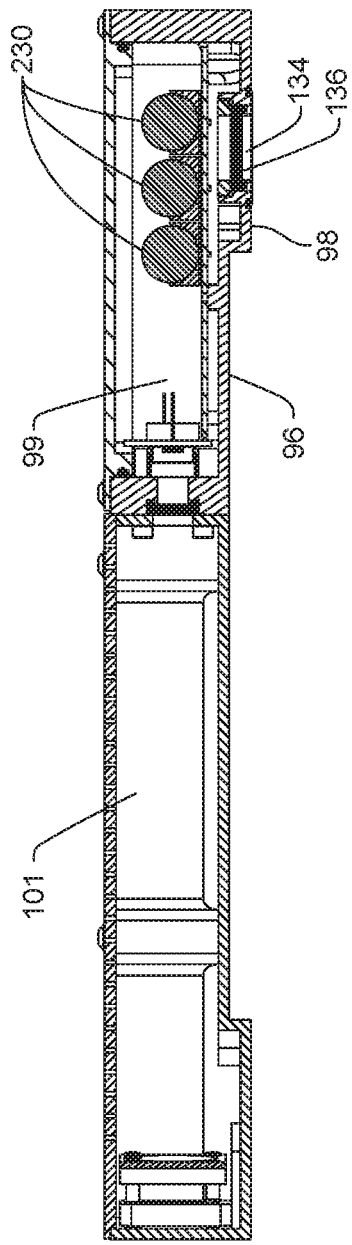

| FIG. 12A | FIG. 12B |

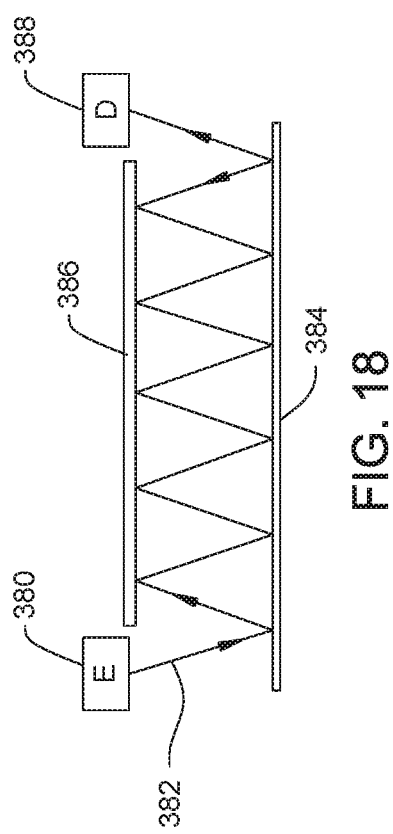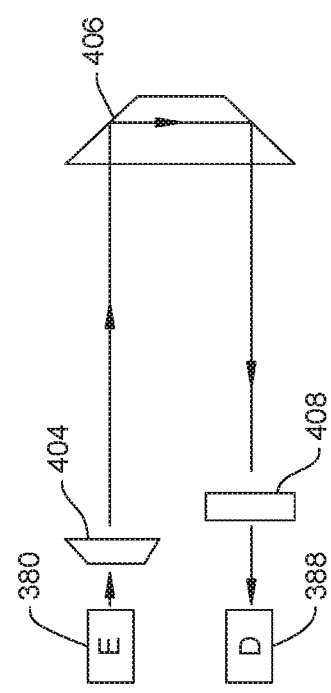

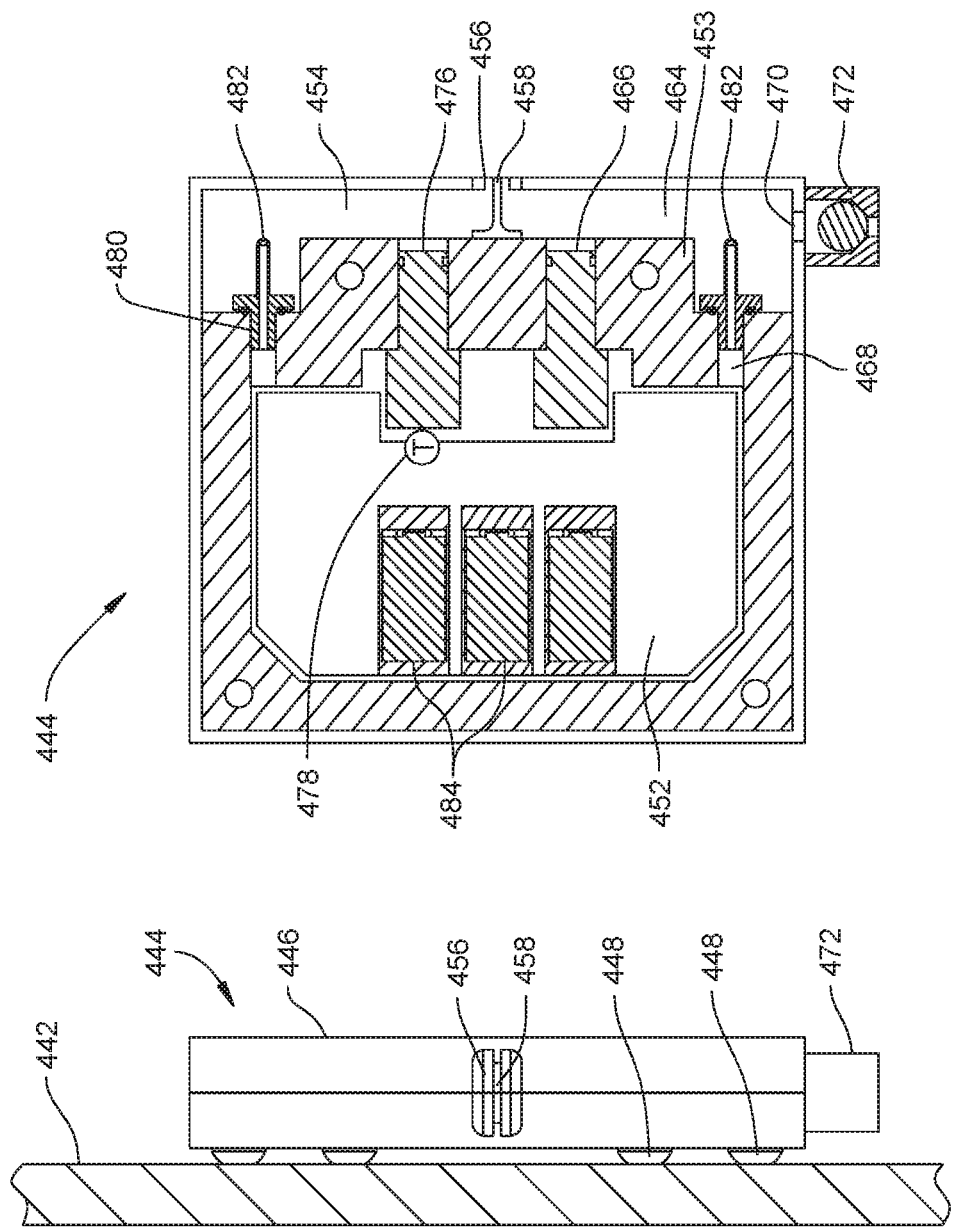

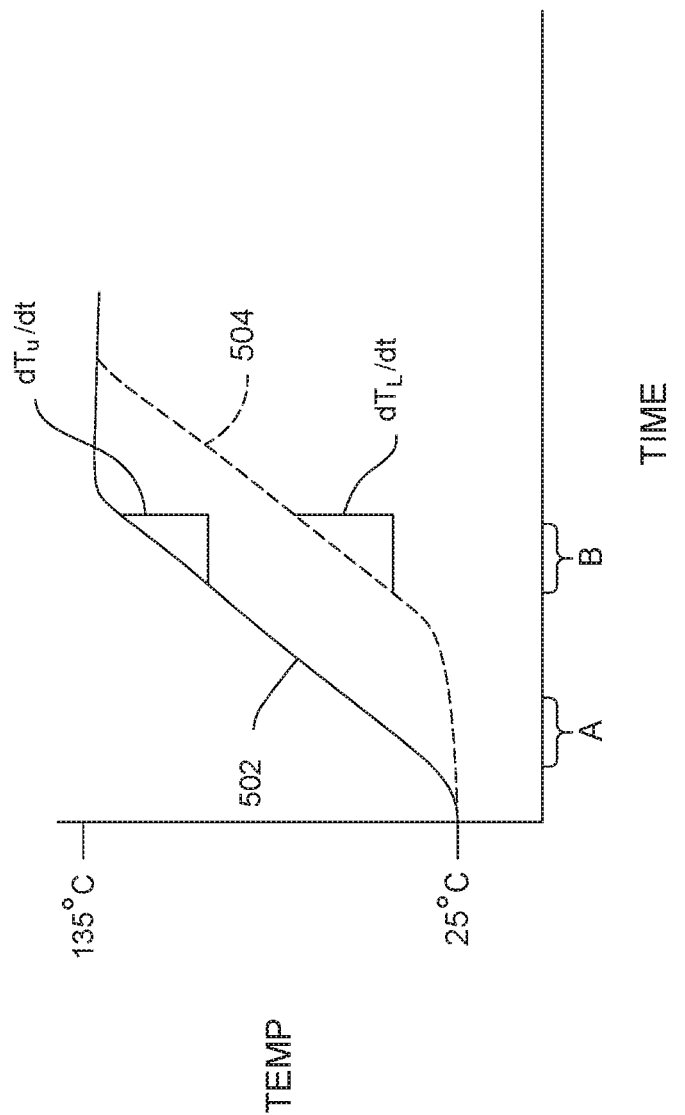

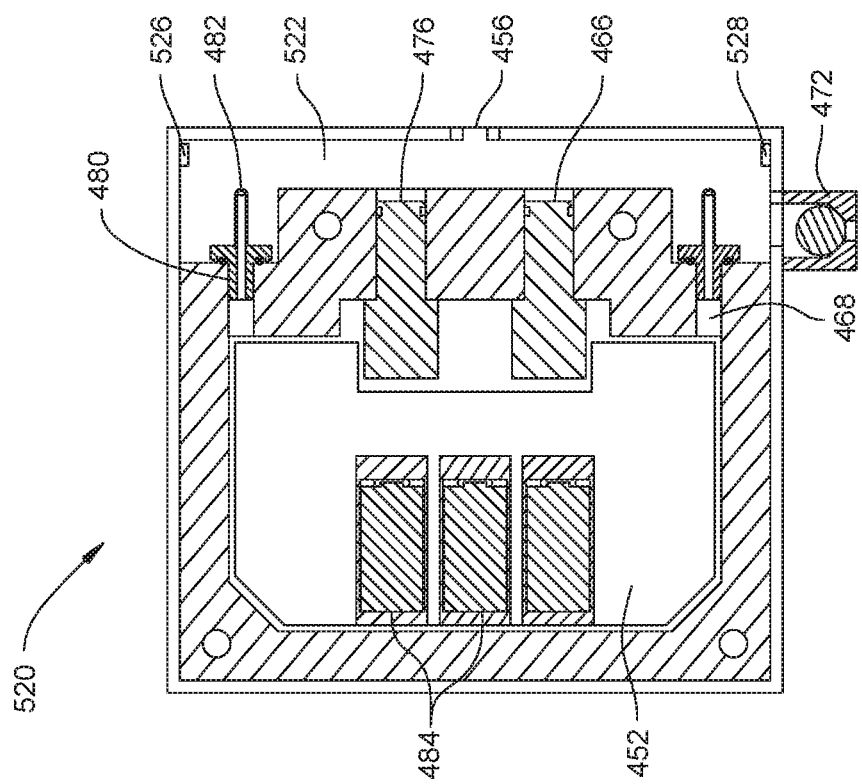

STERILIZATION CONTAINER WITH BATTERY POWERED SENSOR MODULE FOR MONITORING THE ENVIRONMENT IN THE CONTAINER

CROSS-REFERENCE TO RELATED APPLICATIONS

The present application is a divisional of U.S. patent application Ser. No. 15/259,213 filed on Sep. 8, 2016, which is a continuation of PCT International Application No. PCT/US2015/019724 (Intl. Publ. No. WO 2015/138461) filed on Mar. 10, 2015, which claims priority to U.S. Provisional Patent Application No. 61/951,178 filed on Mar. 11, 2014. The aforementioned applications are hereby incorporated by reference in their entirety.

FIELD OF THE INVENTION

This application is generally related to sterilization containers that hold one or more surgical instruments when the instruments are subjected to sterilization.

BACKGROUND OF THE INVENTION

This application incorporates by reference the contents of U.S. Prov. Pat. App. No. 61/779,956, filed 13 Mar. 2013, the contents of which are published in WO 2014/159696 A1/US Pat. Pub. No. US 2015/0374868.

The incorporated by reference publication discloses a sterilization container with a set of sensors and a processor. The sensors are configured to measure the characteristics of the environment in the antimicrobial barrier container. Signals representative of these measurements are sent to the processor. The processor evaluates these container environmental measurements. Using methods disclosed in the referenced publication, the processor verifies whether or not the instruments were properly sterilized. The processor then causes an indication regarding the sterilization state of the instruments to be output.

By using the above-described container, a medical facility is able to essentially almost immediately after the sterilization process, know whether or not the instruments were properly sterilized. This is more efficient than many sterilization systems which require the instruments to be held in quarantine for periods ranging from 3 to 48 hours in order to obtain the results of tests run to determine the state of sterilizing machine's operating characteristics that affect instrument sterility.

The above-described container includes a battery. The battery supplies the charge required to activate the processor as well as the typically one or more sensors that require electrical power to function. The system of the incorporated by reference publication does not disclose any means to minimize the current draw on the battery. This would lead to having to take the sterilization container out of service on a frequent basis in order to either replace or recharge the battery.

Further, for some sterilization processes it is desirable to determine whether or not the instruments in the container are in a saturated steam environment. A saturated steam environment is one in which the majority of the gas in the chamber is water vapor (steam) with only trace amounts of the gases that normally make up air.

This determination is desirable because many instruments do not have unbroken smooth outer surfaces. An instrument may have one or more bores, notches or slots that have a closed end. These closed ends reduce contact with saturated steam on all surfaces of the instrument. Owing to the closed end nature of these void spaces, air may become trapped in these spaces. Due to the tendency of the air to be trapped in these spaces, it has proven difficult to determine whether or not an instrument is therefore completely surrounded by saturated steam.

BRIEF DESCRIPTION OF THE DRAWINGS

FIG. 5 is a longitudinally extending cross section view through the sensor module.

FIG. 18 is a diagrammatic depiction of a first alternative means of directing light in the sensor module internal to the sterilization container of this invention;

FIG. 19 is a diagrammatic depiction of a second alternative means of directing light in the sensor module internal to the sterilization container of this invention;

FIG. 20 is a side view depicting how another sensor module of this invention is attached to a sterilization container; and FIG. 21 depicts the interior of the sensor module of FIG. 20;

FIG. 23 depicts how the principle of why the temperature of components internal to the sensor module of FIG. 22 can be used to determine whether or not the sterilization container to which the sensor module is mounted is full of saturated steam; and FIG. 24 is view depicting the interior of a second alternative version of the sensor module of FIG. 21.

DETAILED DESCRIPTION

I. Sterilization Case with First Sensor Module

Figure 1:
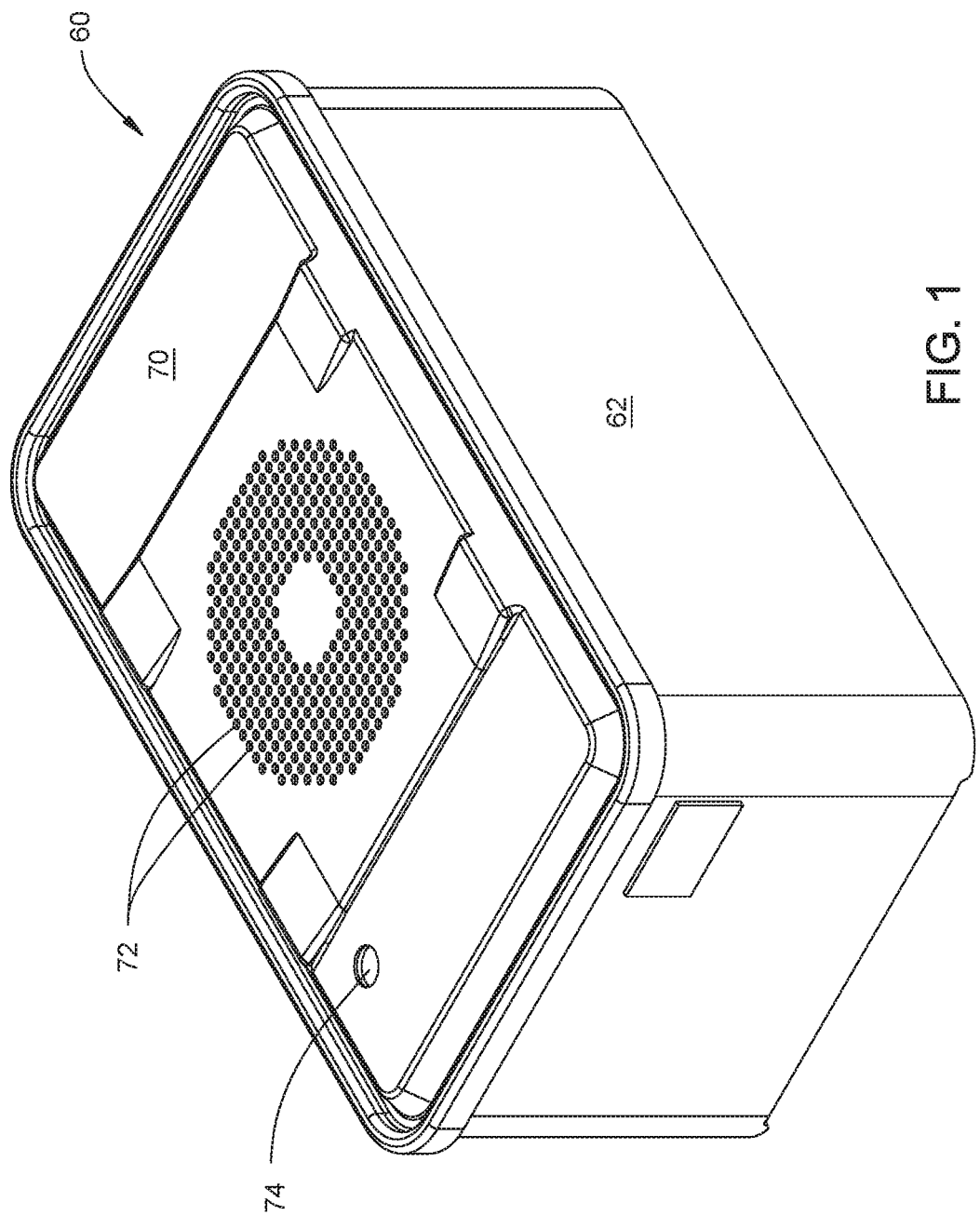
FIG. 1 is a perspective view of the outside of a sterilization container of this invention.
Figure 2:
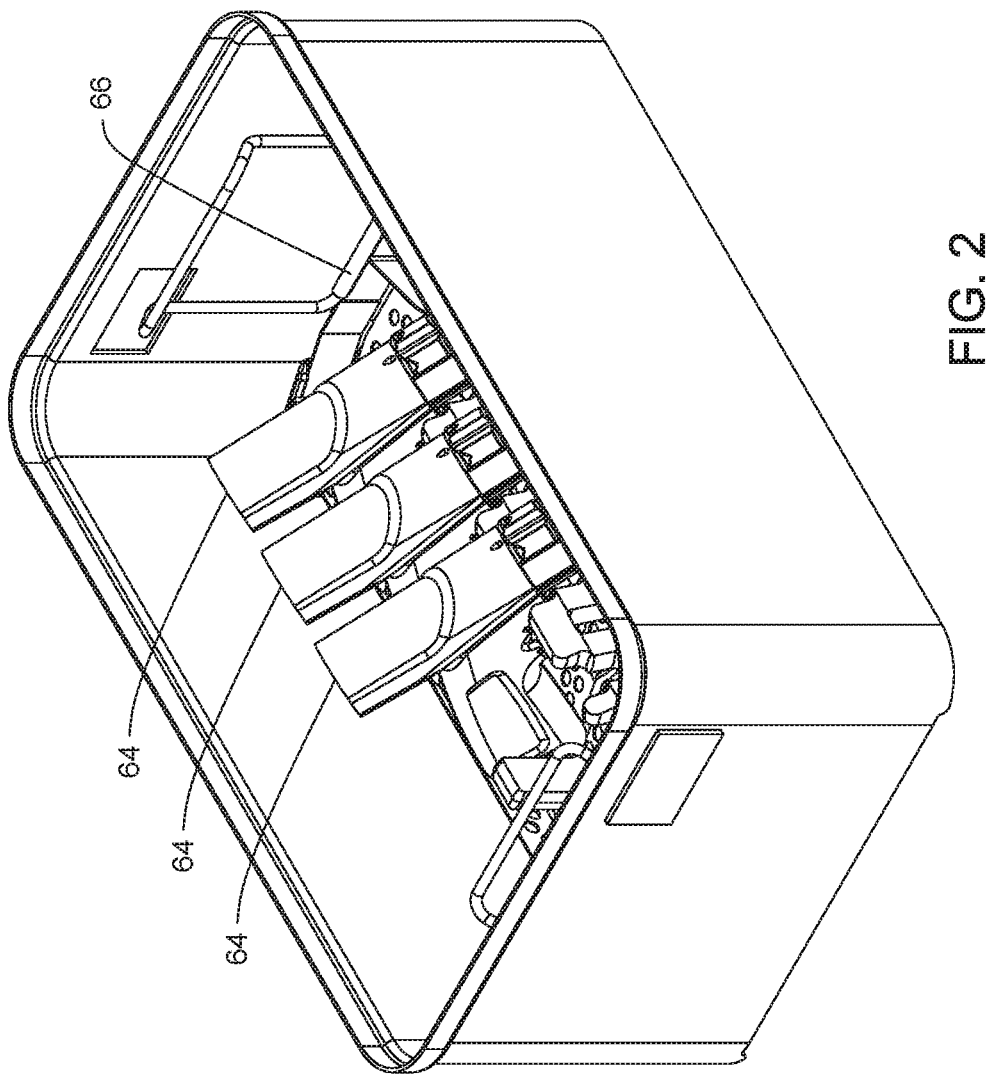
FIG. 2 is a perspective view the inside of the body of the container showing surgical instruments disposed inside the container.

A sterilization container 60 of this invention is now described by initial reference to FIGS. 1 and 2. The container 60 is formed from material that can be placed in a sterilizer and withstand the exposure to sterilants used to sterilize surgical instruments. Container 60 includes a body 62 that is generally rectangularly shaped. Not identified are the front, rear, side and bottom panels that form the body 62. The body 62 is closed at the bottom and open at the top. The body 62 is shaped to hold one or more surgical instruments 64. The instruments 64 are seated on a rack 66 that is removably seated in the body 62. A lid 70 is removably latched over the open top end of the body 62. The lid 70 is formed with openings 72. The openings 72 are openings into the container interior where sterilant is able to flow into and be withdrawn out of the container 60. Not shown is the filter assembly mounted to the inner surface of lid 70. This filter assembly is designed to allow the flow of sterilants in and out of the openings 72 while preventing airborne contaminates from entering the container 60 through the openings. The lid 70 is formed with an additional opening 74 that is spaced from the openings 72. A window is disposed in opening 74 that allows transmission of visible light. The container 60 system described forms a barrier around the instruments that allows sterilant to enter and exit the container interior but prevents containments from entering the container. This barrier can be characterized as an antimicrobial barrier or a Sterile Barrier System (SBS).

Figure 3:
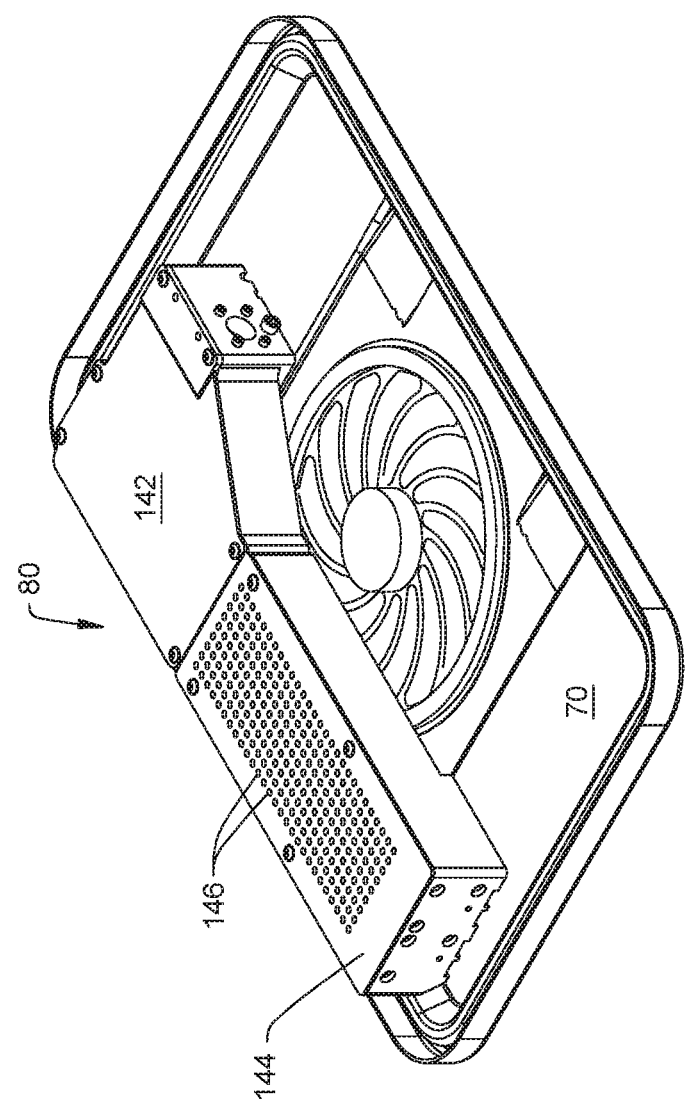
FIG. 3 is a perspective view of the inner surface of the container lid and the sensor module mounted to the lid.
Figure 4:
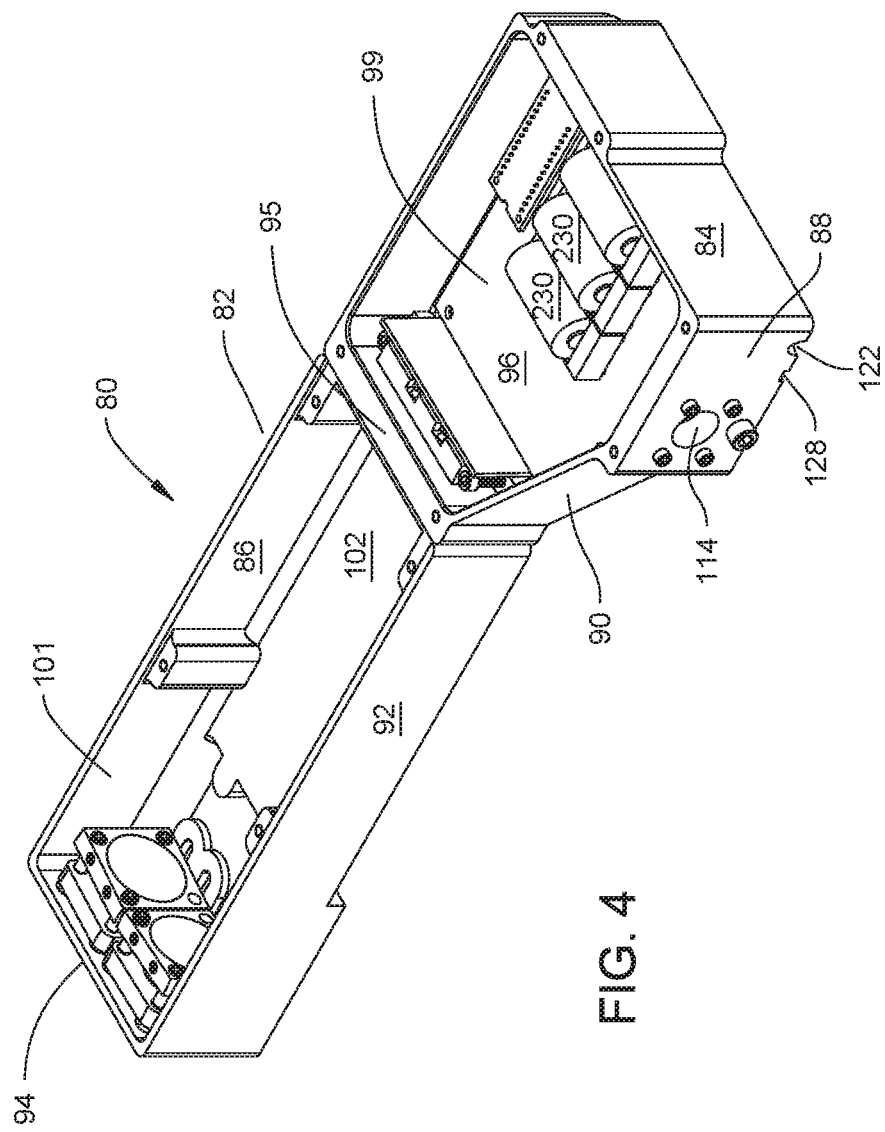
FIG. 4 is a perspective view of the control module with the module covers removed.

The sterilization container 60 of this invention includes a sensor module 80. In the illustrated version of the invention as seen in FIG. 3, the sensor module 80 is shown attached to the inner surface of the container lid 70. In FIGS. 4-10, for ease of understanding the invention, the sensor module 80 is shown inverted from the position of the module when mounted to the container lid 70. The sensor module 80 has a shell or frame 82. Frame 82 consists of a number of panels that define the perimeter of the frame. Arbitrarily these panels include opposed front and rear panels 84 and 94, respectively. Front panel 84 is longer in length and parallel to rear panel 94. A substantially planar first side panel 86 extends between front panel 84 and rear panel 94 on one side of the frame 82. Three side panels 88, 90 and 92 form the side of the frame 82 opposite panel 86. Panel 88 extends perpendicularly rearwardly away from the front panel 84. Panel 88 extends approximately one-fifth the length of the frame 82. Panel 90 tapers inwardly from the rear end of panel 88. Collectively panels 88 and 90 extend approximately one-third the length of the frame 82. Side panel 92 extends rearward from the free end of side panel 90 to rear panel 94. The frame 82 is formed so that side panel 92 is parallel to side panel 86 and perpendicular to the rear panel 94.

The frame is formed so that the bottom edges of the side panels 88 and 92 are elevated. More particularly, these edges are elevated where the panels extend over the lid openings 72. This dimensioning facilitates the insertion and removal of the filter elements over the openings, as seen in FIGS. 1 and 2. The void space between the inner surface of lid 70 and panels 88 and 92 also functions as a through path that allows sterilant to flow through lid openings 72 over the sensor module 80 and into container body 62.

The frame 82 is further formed to have a web 95. The web 95 extends laterally across the frame between opposed side panels 86 and 92. The web 95 is located immediately rearward of where panel 92 extends rearward from panel 90. In some versions of the invention the frame is formed as a two piece structure where two planar panels form abutting portions of web 95. Not shown are the fasteners that hold the panels together.

Frame 82 further includes two base panels. A first base panel, panel 96, extends between front panel 84 and web 95 and between side panel 86 and side panels 88 and 90. Base panel 96 is formed to have a foot 98 that, as seen in FIG. 5, that is recessed relative to the main portion of the base panel.

The second base panel, panel 102, extends rearward from web 95 towards rear panel 94. Base panel 102 extends between side panels 86 and 92. While the base panel 102 extends towards the rear panel 94, base panel 102 does not abut the rear panel 94. Instead, the base panel 102 stops at a location forward of the rear panel 94 so as to define a gap 103, identified in FIG. 6, in the frame between the two panels 94 and 102. Gap 103 allows the circulation of gases and liquids in the sterilization container into the portion of module 80 defined by panels 86, 92, 94, 102 and web 95.

Figure 6:
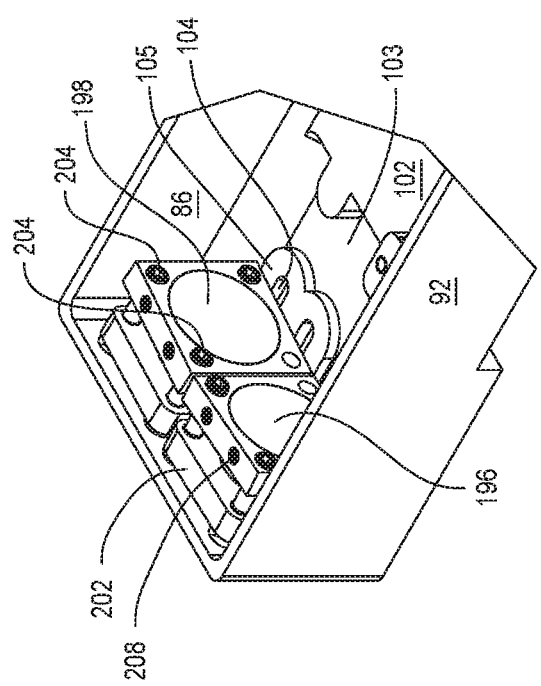
FIG. 6 is a perspective view of the rear end of the sensor module.

Two tabs 105, one seen in FIG. 6, extend forward from the bottom edge of rear panel 94. Each tab 105 is formed with two parallel slots 104. Slots 104 terminate at a location rearward of the forwardly directed free ends of the tabs 105.

When the sensor module 80 is mounted to the container lid 70, the bottom surfaces of the front panel 84, side panel 86, the rear section of side panel 92, the rear panel 94 and foot 98 are disposed against the inner surface of the lid 70. The means by which the sensor module 80 is attached to the lid 70 is neither illustrated nor part of the present invention.

Figure 7:
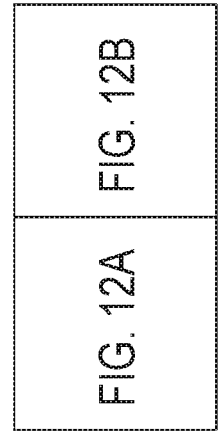
FIG. 7 is a cross sectional view of how the pressure transducers are mounted to the sensor module.
Figure 12:
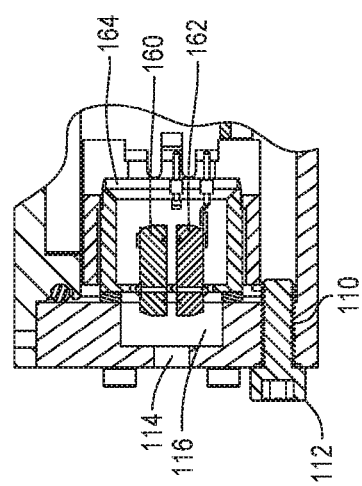
FIG. 12 is an assembly diagram depicting how
Figure 10:
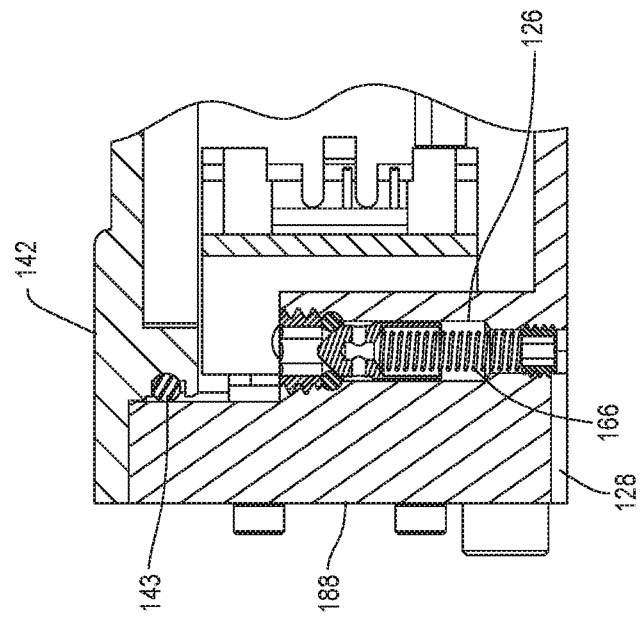
FIG. 10 is a cross section view of how the pressure relief valve is mounted to the sensor module.

The frame 82 is formed with a number of openings. A number of these openings are in the frame side panel 88. Two of the frame side panel 88 are openings are seen in FIG. 7. A first one of the openings, opening 110, extends laterally through the side panel. Opening 110 is threaded. A screw 112 seen in FIG. 10 is normally seated in opening 110 so as to seal the opening closed. The second opening seen in FIG. 7 includes a port 114. Port 114 is circular in diameter and extends inwardly from the outer face of the side panel 88. Port 114 opens into a bore 116 that extends to the inner surface of side panel 88. Bore 116 has a cross sectional area greater than then that of port 114.

Figure 8:
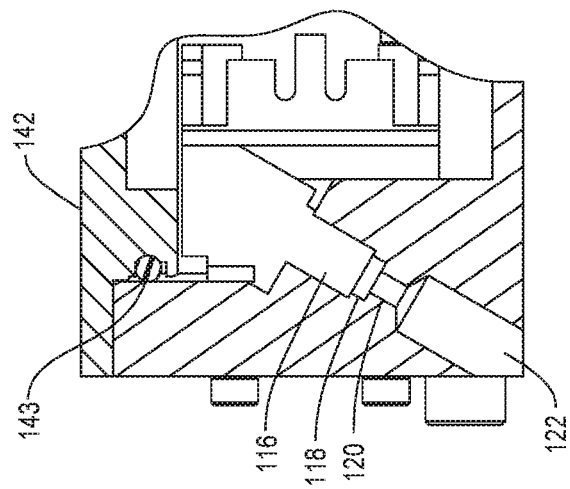
FIG. 8 is a cross sectional view of the bores in which a temperature sensor is seated.

A third opening in side panel 88 is seen in FIG. 8. This third opening consists of four contiguous bores 116, 118, 120 and 122 that extend coaxially and diagonally through the side panel 88. Bore 116 extends downwardly and outwardly from the inner surface of the side panel 88. While not illustrated, the surface of the panel 88 that forms bore 116 is threaded. Bore 118 extends inwardly from the end of bore 116. The side panel 88 is formed so that bore 118 is smaller in diameter than bore 116. Bore 120 is smaller in diameter than bore 118 and extends outwardly and downwardly from bore 118. Bore 122 extends from bore 120 to the outer surface of the side panel 88. More particularly bore 122 opens up in the corner of the frame defined by the outer surface of the side panel and the adjacent perpendicular surface of the bottom of the panel. The side panel 88 is formed so that bore 122 has a diameter that is larger than the diameter of bore 120.

From FIG. 10 it can be seen that side panel 88 includes a fourth opening. This opening consists of a set of contiguous bore sections that collectively are identified as a single bore 126. The adjacent bore sections that form bore 126 differ regarding whether or not they are threaded or smooth and in diameter. The bores of bore 126 are formed in a section of the side panel 88 that is stepped so as to have a lower top than the outer section of the panel. Bore 126 opens into the bottom of the side panel. A groove 128 in the undersurface of the side panel extends from the base of bore 126 to the outer surface of the side panel.

Figure 11:
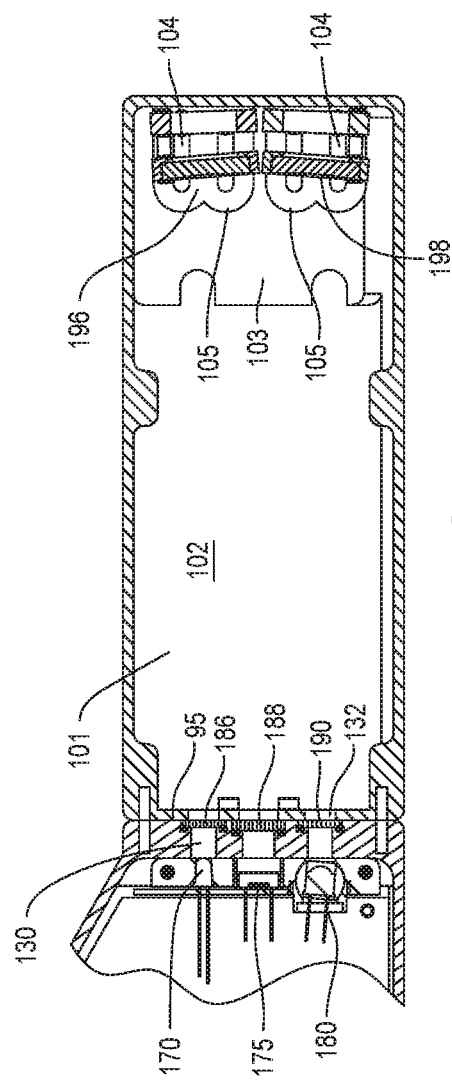
FIG. 11 is an enlarged cross sectional view of a portion of the sensor module.

Three openings extend through web 95 as seen in FIG. 11. Each opening consists of a bore 130 and a recess 132. Only one of each of the bores 130 and recesses 132 are identified. The bores 130 extend rearward from the surface of the web that faces front panel 84. The recesses 132 extend forward from the surface of the web 95 that faces the rear panel 94. Each recess 132 extends to a complementary bore 130. Each recess 132 subtends a cross sectional area greater than that of the complementary bore 130 In version of the invention wherein web is formed from two abutting panels, bores 130 are formed as through openings in one panel and recesses 132 are formed as through openings in the second panel.

The frame base panel 96 is formed with an opening 134 seen in FIG. 5. The opening 134 is formed in the panel foot 98. The sensor module 80 is formed so that when the module is attached to the complementary container lid 70, the opening 134 is in registration with the complementary sealed window 74 in the lid 70. A window 136 is sealed to frame to prevent sterilant from entering the void space 99 defined partially by the base panel 96. Window 136 is transparent to the type of energy emitted by a transmitter integral with the module. In the currently described version of this invention this energy is photonic energy, namely visible light. Accordingly, in this version of the invention the window 136 is transparent to visible light.

Frame 82 is formed with additional openings that accommodate fasteners. Some of these fasteners hold panels and other parts of the frame 82 to each other. Other ones of these fasteners hold components mounted in the frame 82 to the frame. The openings in which these fasteners are fitted are neither described nor identified. Also not called out are the sections of the frame where the panels are relatively thick in order to accommodate these openings and provide added structural strength to the frame.

Two covers 142 and 144 are secured over the frame 82. When the module 80 is disposed in the sterilization container with which the module is used it is understood that the covers 142 and 144 project downwardly from the container lid 70. Cover 142 extends over the void space 99 in the frame defined by the front panel 84, the portion of side panel 86 adjacent the front panel, side panel 88 and web 95. Cover 142 is removably held to the frame by fasteners not identified. The cover 142 is held to the frame so that the void space below the cover is sealed from exposure to gases that are introduced into the container during a sterilization process. These gases, depending on the sterilization process, can include one or more of the following: water vapor (steam); hydrogen peroxide; ethylene oxide; and ozone. To provide this seal an O-ring 143, identified in FIG. 10, is sandwiched between the frame 82 and the cover 142.

Cover 144 extends over the portion of the frame that extends rearward from web 95. Thus the cover 144, front-to rear, extends between web 95 and rear panel 94. Side-to-side the cover 144 extends between the portion of side panel 86 located rearward of web 95 and side panel 92. Cover 144 is formed with openings 146. Openings 146 and gap 103 adjacent frame panels 94 and 102 allow sterilants introduced into the sterilization container to circulate the space 101 in the container defined by panels 86, 92, 94 and web 95. The cover 144 also prevents inadvertent contact with the components of the sensor of module 80 disposed in the space 101.

Figure 9:
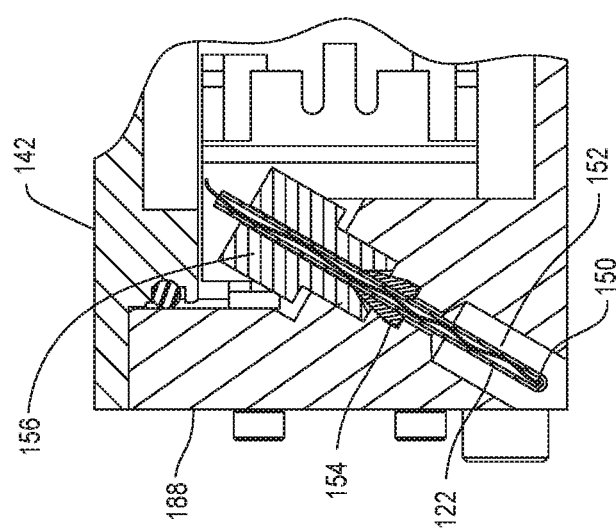
FIG. 9 is a cross sectional view of how a temperature sensor is mounted to the module.

Sensor module 80 includes a temperature sensor the assembly of which is now described by reference to FIG. 9. The actual temperature sensitive transducer is a thermistor 150. Thermistor 150 is encased in a tube 152 formed from material that is thermally conductive and will not corrode when exposed to the sterilants introduced into the sterilization container. In some versions of the invention tube 152 is formed from aluminum. Tube 152 is closed at the outer end, the end of the tube that projects out of frame 82. The tube 152 also has a diameter less than the diameter of frame bores 116, 118, 120 and 122. The tube 152 has a wall thickness that is relatively thin so as to facilitate the rapid conduction of heat through the tube and to the thermistor. In versions of the invention in which the tube is formed from aluminum, the tube may have a maximum wall thickness of 0.2 mm. In another embodiment, the thermistor is potted to the tube walls with a thermally conductive material.

Thermistor 150 and tube 152 are seated in frame bores 116, 118, 120 and 122. Not identified is the wire that extends from thermistor 150 out of the open end of tube 152. More particularly, tube 152 extends through a ferrule 154 and a fitting 156, both of which are made from plastic with a low thermal conductivity, a thermal conductively lower than that of tube 152. Ferrule 154 has a circular base, not identified, that is seated against the step that forms the transition between bores 118 and 120. The ferrule has a head that is conically shaped that extend from the base into bore 116. A bore, not identified, extends through the ferrule. The fitting 156 has a threaded stem and a head that is larger in diameter than the stem. The fitting stem is dimensioned so the fitting threading can engage the threading around bore 116. A bore, not identified, extends axially through the fitting 156. The fitting 156 is further formed so that at the end of the stem, the bore opens into a conically shaped counterbore.

The temperature sensor assembly is attached to the sensor module 80 by placing the thermistor 150 in the closed end of tube 152. Not seen are the conductors that extend to the thermistor. The ferrule 154 is seated in bore 120 and tube 152 inserted through the bore in the ferrule 154. Fitting 154 is threaded into bore 116. The initial positioning of the fitting 154 in bore 116 results in the positioning of the tube 152 in the bore that runs through the fitting. The screwing of the fitting 156 into bore 116 compresses the fitting against the ferrule 154. The compression of fitting 156 against the ferrule causes the ferrule 154 to both compress inwardly around tube 152 and outwardly against the wall of the frame 82 that defines bore 118. This compression of the ferrule 154 thus creates a vacuum tight seal between the frame 84 and the tube 152 and securely holds the tube to the frame.

When sensor module 80 is assembled, the closed end of the tube 152 is spaced inwardly from the inner cylindrical wall of the frame 82 that defines bore 122. This ensures that sterilant circulates freely around the end of the tube, the portion of the tube in which the thermistor 150 is located. Further, owing to ferrule 154 and fitting 156 being formed of material that has a relatively low thermal conductivity, tube 152 is to some extent thermally isolated from module frame 82. This minimizes the extent to which the temperature of the thermistor is affected by the temperature of the frame 82. The thermistor 150 acquires a temperature that essentially is identical to the temperature of the environment inside the sterilization container. Also, when the sensor module 80 is assembled, the tube 150 in most versions of the invention does not project outside of bore 122. This substantially eliminates the likelihood that an instrument in the container or the misplacement of finger can potentially damage the tube that, owing to the thinness of its wall, is relatively fragile.

Two pressure sensitive transducers 160 and 162, manometers, are mounted to the inner surface of frame side panel 88 as seen in FIG. 7. Transducers 160 and 162 are located adjacent panel bore 116. A shell 164 is disposed around the transducers 160 and 162. The shell 164 is secured to the side panel 88 so there is a hermetic seal at the interface between the surface of the panel and the shell. Since the seal extends circumferentially around the portion of the panel 88 that defines bore 116, the seal prevents the fluids (liquid and gaseous) in the container from entering the void space in the module beyond the shell 164.

In some versions of the invention, both pressures sensors 160 and 162 are capacitor type transducers. The capacitance of the sensor 160 or 162 varies as a function of the ambient absolute pressure. A first one of the sensors, arbitrarily sensor 160, provides relatively accurate measurements of ambient absolute pressure for relatively high pressures. For the purposes of this invention a high pressure is a pressure above a minimum pressure of 20 to 50 Torr. The second pressure sensor, sensor 162, provides relatively accurate measurements of absolute pressure for relatively low pressures. For the purposes of this invention, a relatively low pressure is a pressure below a maximum pressure of between 10 and 100 Torr. Pressure sensor 162 provides accurate measurements of pressure to a pressure of 0.5 Torr, more ideally to at least 0.2 Torr and more ideally still to 0.05 Torr. Not shown are the conductors that extend from sensors 160 and 162 through shell 164.

A one-way pressure-trigged valve 166, seen in FIG. 10 is mounted in the bores that collectively form bore 126. Valve 166 opens when the pressure in frame void space 99 is greater than the ambient pressure. In some versions of the invention, the valve 166 is set to open when the pressure difference is between 0.3 and 0.7 Atmospheres. In other versions of the invention, valve 166 is set to open when the pressure difference is between 0.4 and 0.6 Atmospheres.

Valve 166 opens when, during a sterilization process, the container is exposed to an environment in which the pressure is substantially below atmospheric pressure. The opening of valve at least partially reduces the pressure differential between the environment and void space 99. This reduction in pressure difference reduces the mechanical stress on the components forming the sensor module as well as the seals between these components.

After sterilization of the contents of the container is complete, the container is returned to the ambient, room, environment. When the container is in this environment, the pressure in void space 99 is less than the ambient pressure. This pressure difference is typically less than 0.4 to 0.6 Atmospheres. This pressure difference does not induce appreciable mechanical stress in the components forming the sensor module 80.

There may be times during the life of the sensor module 80 when it is necessary to access the components in void space 99. To so access these components, screw 112 is removed from bore 110. The removal of screw 112 allows the pressure in the void space to equalize with the ambient air pressure. This reduces the effort required to remove cover 142.

Two light emitting devices 170 and 180, are attached to web 95. In some versions of the invention, devices 170 and 180 are LEDs. The LEDs 170 and 180 are each mounted in a separate one of the bores 130 formed in the web 95. Each LED emits light that includes light at wavelength that is absorbed by one of the gases or vapors that may be present inside the container 60 during a sterilization process. Two gases, vapors, that may be introduced into the container may be vaporized water and vaporized hydrogen peroxide. Versions of the sensor module 80 designed for use with this container will have one LED, arbitrarily LED 170 capable of emitting light within a range that includes the 940 nm wavelength, the wavelength of light absorbed by water vapor. The second LED 180 emits light within a range that includes the 245 nm wavelength, the wavelength of light absorbed by vaporized hydrogen peroxide. Both LEDs 170 and 180 are oriented to emit light towards the frame rear panel 94

A photodetector 175 is also attached to web 95. The photodetector 175 is seated in the center located bore in the web 95. Photodetector 175 is capable of emitting a signal that varies as a function of the intensity of the light at wavelengths of the light absorbed by the gases/vapors the concentrations of which are to be measured. The photodetector 175 is positioned in the block so the light detecting surface of the sensor is oriented towards the rear panel 94.

Figure 12A:
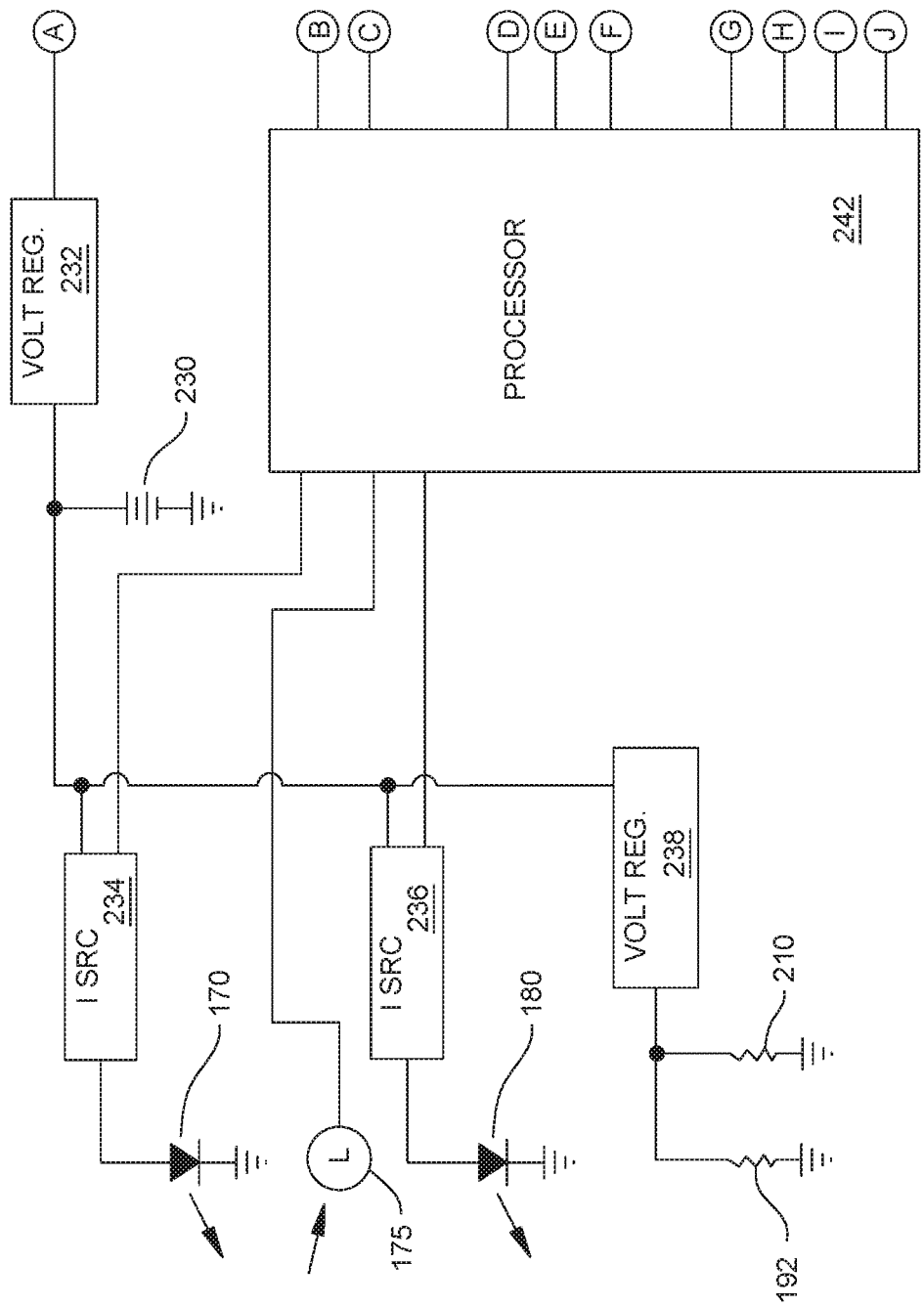
FIGS. 12A and 12B are assembled together to form a block and partial schematic diagram of the electrical components of the sensor module.
Figure 12B:
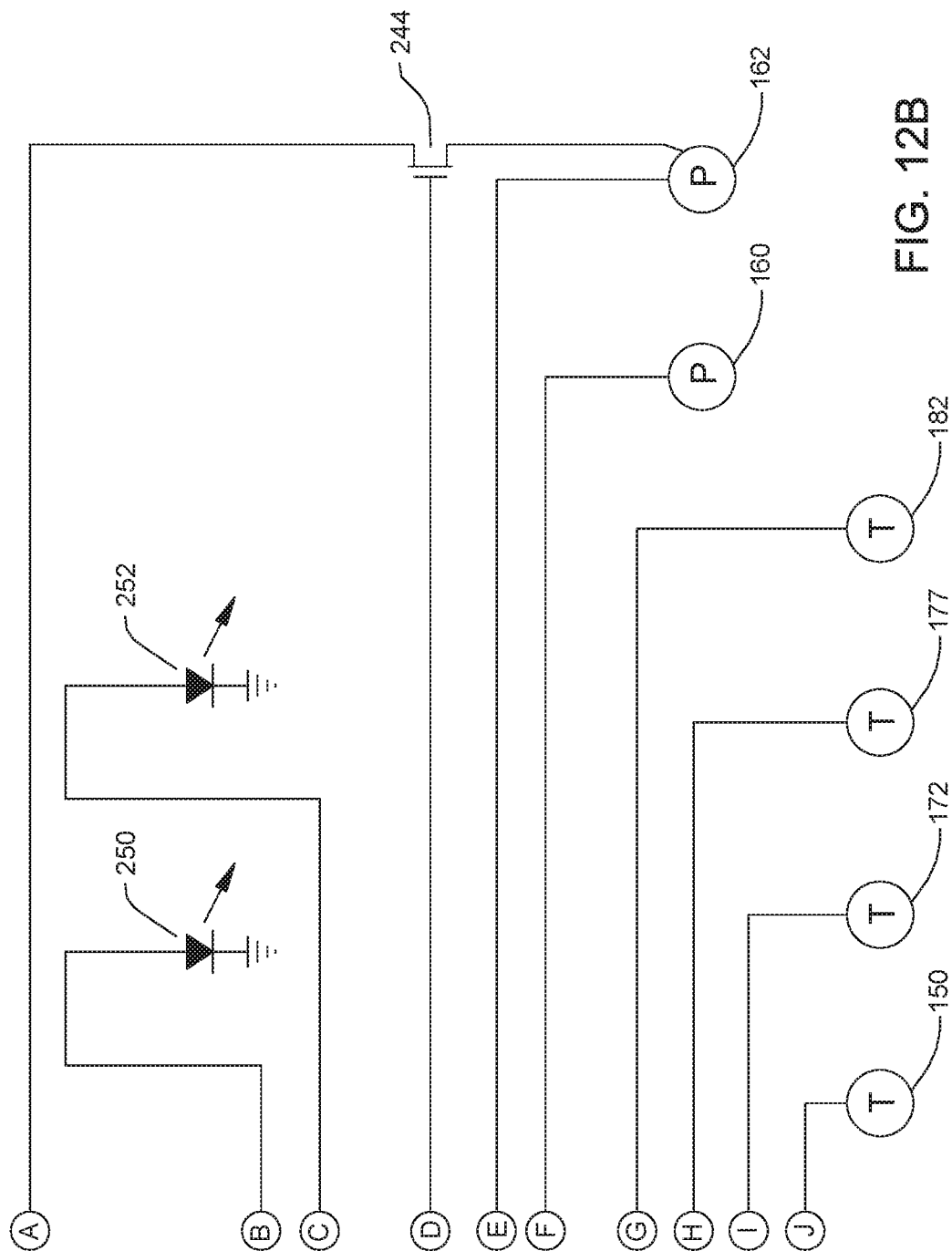

Three temperature-sensitive transducers 172, 177 and 182, shown only in the block diagram of FIG. 12B are also mounted to web 95. In some versions of the invention, transducers 172, 177 and 182 are thermistors. Transducer 172 is mounted to web 95 to provide a measurement representative of the temperature of LED 172. Transducer 177 is mounted to the web 95 to provide a measurement of the temperature of photodetector 175. Transducer 182 is mounted to the web 95 to provide a measure of the temperature of LED 180.

A window is seated in each of the recesses 132 formed in web 95 as seen best in FIG. 11. Each window is mounted to the web 95 in such a way that the window provides a transparent barrier between space 101 and LED 170 or 180 or photodetector 175 covered by the window. A first window, window 186, is seated in the recess 132 disposed around LED 170. Window 186 is formed of material that filters outs substantially all light other than the light absorbed by water vapor. Window 188 is seated in the recess disposed around the photodetector 175. Window 188 is formed from material that is highly transparent to range of wavelengths of the light absorbed by water vapor and the vaporized hydrogen peroxide. Window 190 is seated in the recess 132 disposed around LED 180. In some embodiments, the window 190 is formed from material that filters out substantially all light other than light of the wavelength absorbed by vaporized hydrogen peroxide.

A heating element 192, represented by a resistor in FIG. 12A, is mounted to web 95.

Two concave mirrors 196 and 198 are adjustable mounted to the rear panel 94 of the frame 82. As identified with respect to mirror 196, a fixed plate 202 and a moving plate 206 is associated with each mirror. Each pair of plates 202 and 206 are disposed over one of the tabs 105 that project forward of the rear panel 94. The position of the plates along the tab 105 is adjustably locked by means of set screws (not illustrated) that seats in the tab slots 104. Rigid plate 202 is located between the rear panel 94 and the moving plate 206. Adjustment screws 204 (two screws identified) that extend between plates 202 and 206 allow the angular orientation of the moving plate 206 to be adjusted relative to the fixed plate 202. Each mirror is bonded to, attached to or formed as part of the moving plate with which the mirror is associated. The ability to move the plates along the tabs allows the positions of the mirrors within space 101 to be adjusted. The ability to set the orientation of the moving plates relative to the rigid plates allows the orientation of the mirrors to be adjusted.

Mirror 196 is positioned to reflect the light emitted by LED 170 to the photodetector 175. Mirror 198 is positioned to reflect the light emitted by LED 180 to the photodetector 175. Generally, the components forming the sensor module 80 are selected so that mirrors have focal points that are one-half the distance from where the LEDs 170 and 180 are located to the mirrors.

A heating element 210 is attached to each moving plate 206. In the drawings the heating elements 210 are represented by a single resistor in FIG. 12A. The mean by which the heating elements 210 are attached to moving plate 206 is not part of the present invention.

FIGS. 12A and 12B, when assembled together, form a block and partial schematic diagram of the components of the sensor module 80. These components include a battery 230. The battery 230 that provides the power to the other components of the module. The battery 230 may consist of plural cells, (individual cells not identified.)

A voltage regulator 232 is connected to the battery 230. Voltage regulator 232 provides constant voltages at the appropriate voltage levels to the components internal the module that require these voltages. To avoid the complexity of the Figures, with one exception discussed below, the connections from which the voltages are supplied to the components internal to the module 80 are not illustrated.

Two constant current sources 234 and 236 are also connected to battery 230. Current sources 234 and 236 selectively turned on and off. Current source 234 is the source of the current that is applied to LED 170. Current source 236 is the source of current that is applied to LED 180. Not shown are the load resistors in series with the LEDs 170 and 180.

A selectively turned on/off voltage source 238 is also connected to the battery. The voltage output by source 238 is supplied to heating elements 192 and 210.

Sensor module 80 also contains a processor 242. Processor 242 monitors and records the environmental measurements made by the module transducers. Not identified in the memory integral with the processor 242 in which these measurements are stored. The processor also controls the operation of at least some of the electrically activated components of the module. In some versions of the invention the processor, monitors the environmental characteristics measured by the sensors. Based on the measured environmental characteristics, the processor 242 provides an indication regarding whether or not the surgical instruments disposed in the container 60 were properly sterilized.

In Figures the signals representative of temperatures measured by thermistors 150, 172, 177, and 180 are shown as being applied to processor 242 as input signals. Also applied to the processor as input signals are signals representative of container pressure as output by the pressure transducers, 160 and 162. The signal representative of the light measured photodetector 175 is also sourced to the processor as an input signal.

In the Figures, a connection is shown from voltage source 232 to pressure transducer 162. This is to represent that for each of thermistors 150, 170 177 and 180 as well as the remaining pressure transducer 160 and photodetector 175, a potential is supplied to the transducer in order for the transducer to operate. A switch, represented by MOSFET 244, is in series between the voltage source 232 and the pressure transducer 160. This switch controls the application of the potential required to activate the transducer 160. Processor 242 is shown connected to the gate of MOSFET 244. This is to represent that the processor 242 controls the application of the potential to the pressure transducer 162. While not shown it should be understood that the processor 242 controls the application of the potentials required to energize the transducers and sensor components.

Connections are also shown extending from the processor 242 to current sources 234 and 236 and voltage source 236. These connections represent that the processor 242 controls the sourcing of the current from the current sources 234 and 236 and the on/off state of voltage source 236. The on/off state of voltage source 236 is controlled to, by extension, control the energization of heating elements 192 and 210.

The processor 242 is configured to source data to outside of the sterilization container 60. These data are based on the measurements made by the transducers integral with the sensor module 80. In the illustrated version of the invention, these data are sourced by the selective actuation of two LEDs 250 and 252. LEDs 250 and 252 are mounted in void space 162 so that light they emit is visible through module window 136 and lid opening 74. The LED 250 emits green light. The LED 252 emits red light.

II. Operation

Figure 13:
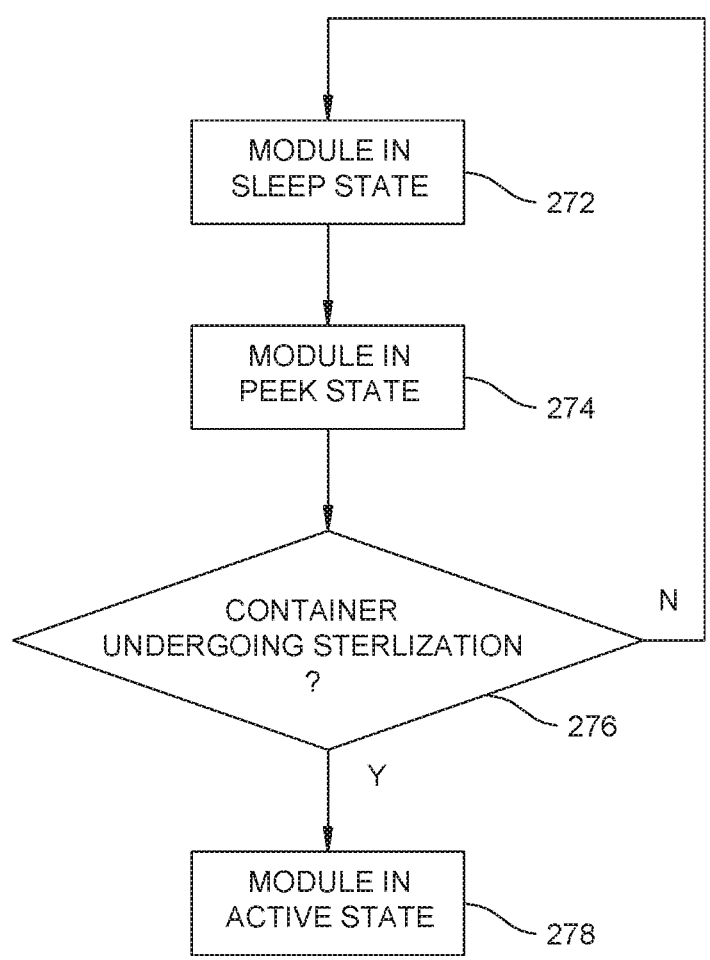
FIG. 13 is a flow chart of the process steps performed by the sensor module as the module cycles through the sleep, peek and active states.

The initial operation of sensor module is now explained by reference to FIG. 13. For the majority of the time the container 60 and, by extension, the module 80, are in an ambient room environment. To conserve the draw of charge from battery 230, the module operates in a sleep state, represented by step 272. When in the sleep state the processor 242 operates in a state in which only minimal power is drawn by the components internal to the module 80. One sub-circuit integral with the processor that does receive power is the clock circuit (circuit not illustrated). When the module is in the sleep state, the potentials needed to activate the temperature, pressure and light transducers are not sourced. Current sources 234 and 236 are in the off state.

Periodically, based on the elapsed time indicated by the clock circuit, the module enters a peek state, step 274. When the module 80 is in the peek state, the processor enters a higher power consuming state than when in the sleep state. When in the peek state, the processor 242 actuates the transducers that provide an indication regarding whether or not the sterilization container 60 may have been placed in a sterilizer and is being subjected to a sterilization process. The transducers that are actuated when the module 80 is in the peek state are the sensors that would provide measurements indicating that, as a result of the initiation of the sterilization process, the environment inside the sterilization container 60 has significantly changed from the room temperature environment. A typical sterilization process starts with either the heating of gases inside the sterilization container 60 or the drawing down of the pressure inside the container. Accordingly, in the execution of the peek state step of this type of the container the processor asserts the command that results in the activation of either the thermistor 150 or pressure transducer 160. The signal representative of the sensed environmental characteristic is applied to the processor 242.

Step 276 represents the evaluation by the processor of the environmental measurement made when the module is in the peek state. For example, if the sterilization process is one in which the initial step of the process is the heating of the container, step 276 is the determining whether or not the container temperature, as measured by thermistor 150 is appreciably above room temperature, for example greater than 35° C. If the sterilization process is one in which the initial step of the process is the drawing of a vacuum in the sterilization container 60, step 276 is the determining whether or not the signal from pressure transducer 160 indicates that the container absolute pressure has dropped to below 690 Torr, approximately 70 Torr below atmospheric pressure.

Processor 242 interprets the evaluation of step 276 testing false as an indication that the sterilization container is not being subjected to a sterilization process. The processor 242 then returns to the sleep state as represented by the loop back to step 272. As part of this loop back the transducer used to determine whether or not the container 60 is being sterilized is turned off and the processor returns to the low power consuming mode. In many versions of the invention, it is anticipated that the module will enter transition from the sleep state to the peek state once every 1 to 3 minutes. The processor will take approximately 50 to 250 milliseconds to make the determination regarding whether or not the sterilization container is being subjected to a sterilization process.

Alternatively, the environmental analysis of step 276 may indicate that the sterilization container is being subjected to a sterilization process. If this analysis tests true, the sensor module 80 enters an active state, step 278. In the active state the processor 242 is in a state in which the processor draws more charge than when in the sleep state. When in the active state, the processor may draw more power than when in the peek state. Also, depending on the time it takes a particular transducer to enter a stable state after being actuated, the processor may assert the control signals that result in the simultaneous application of activation voltages to different transducers. Thus, thermistors 150, 172, 177 and 182 and pressure transducers 160 and 162 may each need to be turned on for a period of at least 1 second before they output steady state signals. In this situation, the processor asserts the signals that cause the simultaneous application of the potentials needed to turn on these transducers simultaneously.

Also as part of the entry into the active state, the processor actuates the heating elements 192 and 210. The heating elements 192 and 210 are actuated by the assertion of command to voltage source 238 that results in the voltage source sourcing energization signals to the heating element 192 and 210. The thermal energy output by heating elements 192 heats the windows 186, 188 and 190. The thermal energy output by heating elements 210 heats the mirrors 196 and 198. The heating of windows 186, 188 and 190 and mirrors 196 and 198 places these components of the module at a temperature that is above the condensation temperature of the vapors inside the container 60. When vapors (gases) are introduced into space 101 the fact that these components are at a temperature above the condensation temperature substantially eliminates the condensation of these vapors on these components.

Figure 14:
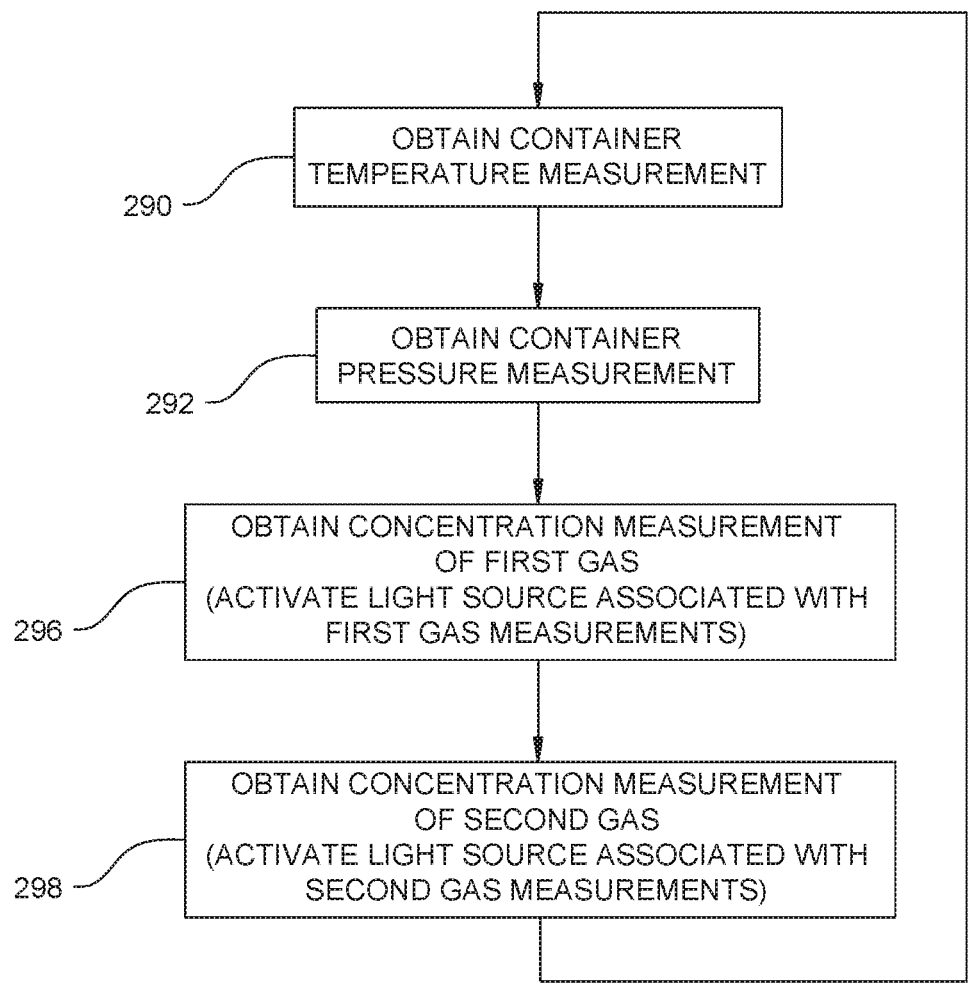
FIG. 14 is a flow chart of the how the sensor module measures the characteristics of the environment in the sterilization container during a sterilization cycle.

FIG. 14 represents the monitoring of the environment inside the container 60 when module 80 is in the active state. Step 290 represents the reading of the signal output from thermistor 150 to determine temperature inside the container 60. Step 292 represents the reading of the signal output from pressure transducer 160 or 162 to determine pressure in the container 60. The pressure reading accepted as container pressure by the processor is a function of the predetermined low boundary pressure. If the pressure is above the low boundary, the signal representative of pressure from transducer 160 is employed as the signal representative of container pressure. If the pressure appears to be at or below the low boundary, the signal representative of pressure sourced by transducer 162 is employed as the signal representative of container pressure.

During a sterilization process different gases may be simultaneously or consecutively introduced into the sterilization container 60. For one sterilization process, it is necessary to obtain essentially simultaneous measurements of the concentrations of water vapor and vaporized hydrogen peroxide in the container. It should be understood that each of the gases for which a concentration measurement may be required may not actually all be sterilants. A particular gas may be a byproduct of the production of the sterilant. Alternatively, the gas may be a gas that exists in the ambient environment. However, to verify the effectiveness of some sterilization processes, it is necessary to know the concentration levels of these gases that do not contribute to the sterilization process. For example, to determine the effectiveness of a process in which hydrogen peroxide is the sterilant, it is desirable to know the essentially simultaneous concentration levels of both the vaporized hydrogen peroxide and the vaporized water in the sterilization case.

The concentration of gas in a space is related to the fraction of light absorbed by the gas in the space at a specific wavelength for that gas. Module 80 of this invention measures the absorption of light at the specific and different wavelengths associated with gases for which it is necessary to determine their concentrations. These measurements start with the not illustrated step of the application of a potential from voltage source 232 to the photodetector 175 to turn on the photodetector. Depending on the particular structure of the photodetector 175, the photodetector may be turned and held on as part of the placing of the sensor module in the active state. Alternatively, as part of the below described steps 296 and 298 the photodetector may be momentarily turned on when each of LEDs 170 and 180 are turned on. In these versions of the invention, the photodetector is typically turned on for at least 50 milliseconds prior to the turning on of the LED 170 or 180.

Step 296 represents the measuring of the concentration of the first gas, here water vapor. Step 296 is executed by processor 242 asserting a signal to the current source 234 that results in the source apply current to LED 170 that results in the emission of light by the LED. The emitted light is transmitted through web 95 and window 186. From window 186 the light is applied to mirror 196. From mirror 196 the light is reflected through window 188 to photodetector 175. The quantity of the light that strikes the photodetector is inversely related to the absorption of light by the water vapor. Therefore, the signal output by the photodetector in step 296 represents a measurement of the concentration of water vapor in the sterilization container. The execution of step 296 concludes with the turning off of current source 234 and the resultant turning off of LED 170.

During the execution of step 296, the processor 242 also asserts the appropriate control signals so the processor is able to obtain the temperature measurements from thermistor 172, the temperature sensor associated with LED 170 and thermistor 177, the temperature sensor associated with the photodetector 175. During the processing of the signal from the photodiode 175, the processor 242 uses these temperature measurements to compensate for variations in the light emitted and the light detected as a result of variations in temperature of the components with which these temperature sensors are associated.

A step 298 is the measuring of the concentration of a second gas, in this example vaporized hydrogen peroxide. In step 298 the processor 242 asserts the command signal to current source 236 that results in the current source turning on. Current source 236, when active, asserts the current to LED 180 required to cause the LED to emit light in the wavelength that is absorbed by vaporized hydrogen peroxide. The light emitted by LED 180 passes through the web 95 and window 190 to mirror 198. The light is reflected by the mirror 198 through window 188 to the photodetector 175. In step 298 the signal output by the photodetector 175 and applied to the processor 242 functions as a measure of concentration of vaporized hydrogen peroxide in the sterilization container 60. Step 298 concludes with the negating of the command signal from the processor 242 that holds current source 236 in the on state. The turning off of the current source 236 results in the turning off of LED 180.

During the execution of steps 296 and 298 processor 242 also asserts the appropriate control signals so the processor is able to obtain the temperature measurements from thermistor 177 and thermistor 182, the temperature sensor associated with the LED 180. During the processing of the signal from the photodiode 175, the processor uses these temperature measurements to compensate for variations in the light emitted and the light detected as a result of variations in temperature.

The sensor module repeatedly makes the above-described measurements of the characteristics of the environment internal to the sterilization container 60. In FIG. 14 this is represented by the loop back from step 298 to step 290-. In practice, the measurements taken during steps 290-298 are taken with a frequency of between 0.25 and 5 Hz and more often at a frequency between 0.5 and 2 Hz. In the period in which any single set of measurements are taken, each LED 170 and 180 is turned on for a phase that last less than 25% of the total period, usually less than 10% of the total period and more ideally less than 5% of the total period. The frequency with which these measurements are taken are understood to be greater than the frequency at which the processor transfers from the sleep state to the peek state.

Figure 15:
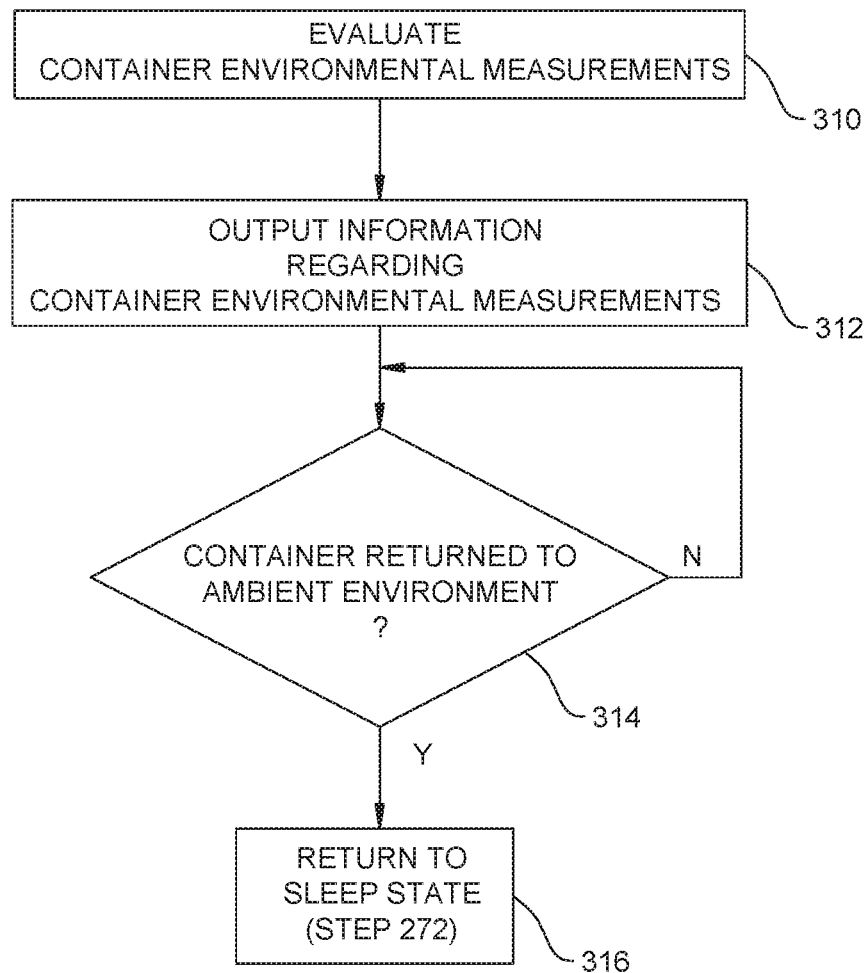
FIG. 15 is a flow chart how the sensor module, evaluates and outputs information based on the container environmental characteristics made by the module.

The evaluation of the container environmental characteristics is now explained by reference to the flow chart of FIG. 15. Initially it should be understood that the steps of evaluating the characteristics are typically integrated with the above-described steps of measuring the environmental characteristics.

Step 310 is the step of evaluating the measured environment characteristics to determine whether or not the sterilization process was satisfactorily completed. The specific sub-steps of step 310 are not part of the present invention. For the purposes of understanding how module 80 function it can be generally understood that the one or more sub-steps of step 310 often involves making at least one comparison of an environmental measurement made by one of the module sensors to a validated process measurement. A "validated sterilization process" is understood to be a sterilization process that, based on past testing, is known to sterilize a particular instrument to a sterility assurance level that essentially ensures any microbial material on the instrument would be innocuous. A surgical instrument is often considered sterilized if the instrument has a sterility assurance level (SAL) of $10^{-6}$. This means there likelihood that if the microorganism population on the instrument was reduced by at least 99.9999%. The incorporated by reference U.S. Prov. Pat. App. No. 61/779, provides an explanation of how to obtain environmental measurements for a validated sterilization process.

A validated sterilization process for the instrument in the container 60 may be one which the instrument is subjected to concentration of 13 mg/l vaporized hydrogen peroxide at a temperature of at least 28° C. for a period of at least 6 minutes. As described in the incorporated by reference U.S. Prov. Pat. App. No. 61/779,956 the data describing these validated sterilization process measurements are preloaded into the memory integral with the processor 242 prior the start of the sterilization process. The means of loading these data are not part of the present invention.

When the above measurements are the validated sterilization process measurements for the instrument, in step 310 the processor evaluates the environmental measurements made by the sensors to determine, if for a period of at least 6 minutes, the vaporized hydrogen peroxide in the container was measured to have a concentration of at least 13 mg/l while the temperature inside the container was at least 28° C.

Step 312 represents the outputting of information by the module based on the evaluations performed in step 310. In the described version of the invention, the processor 242 outputs the information by selectively turning on one of the two LEDs 250 or 252. If the evaluation of step 310 tests positive, then the instrument in the container 60 was sterilized to an acceptable SAL. In this situation the processor 242 asserts the command signal that results the LED 250 emitting green light. A negative result for the evaluation of step 310 is an indication that the there is a likelihood that instrument in the container 60 was not sterilized to an acceptable SAL. In this situation, processor 242 asserts the command signal that results in LED 252 emitting red light. The light the facility personnel see emitted through module window 136 and lid opening 74 thus provides an indication regarding whether or not the instrument in the container was acceptably sterilized.

Step 314 is the evaluation by the processor to determine whether or not the sterilization container 60 was removed from the sterilizer and return to an ambient environment, sometimes called a room environment. The evaluation of step 314 may be performed by the continued measuring of the container temperature and pressure. In one implementation of the invention the processor interprets environmental measurements that the container has been at room temperature and room pressure for a period of time of at least 10 minutes as an indication that the sterilization process is completed and the container and the instrument in the container back in a room environment. The loop back if this evaluation tests negative represents that the processor 242 repetitively makes the evaluation of step 314 until the evaluation tests positive.

After some elapse of time after the sterilization process is completed, the evaluation of step 314 tests positive. Processor 242 responds to this positive test by in step 316 by placing the module in the sleep state. The module returns to step 272. The processor stops the sourcing of power to the transducers that is required in order for the sensors to make the required active state environment measurements. After a sterilization process is completed and the module returns to the sleep state the appropriate LED 250 or 252 remains on. This provides an indication of whether or not the instrument 64 in the container 60 has been properly sterilized.

Sterilization container 60 of this invention provides data regarding the environment inside the container while the container and the one or more instruments in the container are being sterilized. The container relies on a battery 230 integral with the container source the power needed to operate the sensors and data logging components in the container. This eliminates the need to, when the container is in a sterilizer, provide a power connection from the sterilizer to the container. During the large blocks of time the sterilization container is not subjected to a sterilization process, the power drawn by the power consuming components in the container is kept to a minimum. When the container is subjected to a sterilization process, the power required to actuate at least some of the environmental sensors is only supplied to these sensors in spaced apart duty cycles. The cumulative time of these individual duty cycles is less than the time period required to perform the sterilization process. This regulating of when the sensors internal to the sterilization case are energized conserves the charge stored in the battery 230. The conservation of battery charge reduces the frequency with which the battery 230 needs to be replaced or recharged.

Further some light emitting components have a life time that is at least partially a function of the amount of time the components are actuated. By not always actuating the light emitting components associated with vapor measuring assemblies, the lifetimes of the components can be extended.

Container 60 of this invention is further designed so that a single photodetector 175 is all that is required to measure the concentrations of plural different gasses and vapors. This embodiment of the invention eliminates the need to provide a separate photodetector for each wavelength of the light that intensity of which should be measured. This feature of the invention eliminate more than the cost of the plural photodetectors. This feature of this invention also eliminates the need to provide space for plural light paths so the light emitted by each light source travels to a detector specific for that light source.

III. Alternative Method of Determining Gas Concentration

Figure 16:
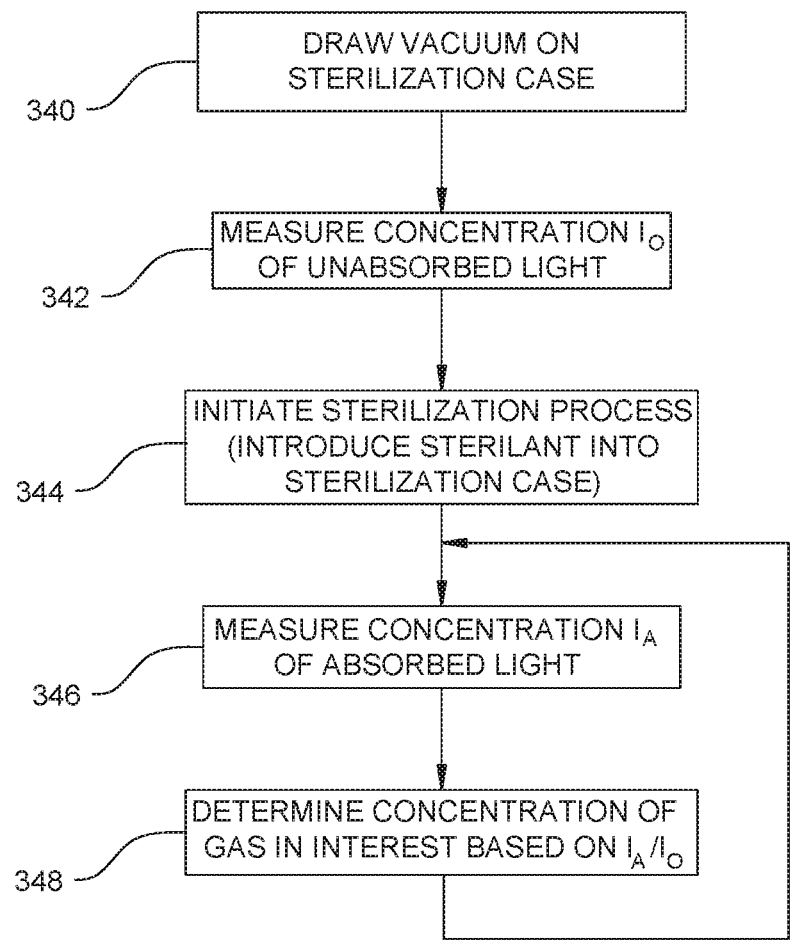
FIG. 16 is a flow chart of an alternative method of determining gas concentration as a function of absorbed light with the sterilization container of this invention.

An alternative means of determining the concentration of the gas (or gasses) for which this information is needed to evaluate the effectiveness of the sterilization process is now described by reference to FIG. 16. The process of FIG. 16 is explained by reference to how the concentration of hydrogen peroxide gas can be determined. The method may be integrated with the methods of FIGS. 13-15. In this method of the invention, the sterilization container 60 is initially placed in the sterilizer (step not shown). Prior to the introduction of any sterilizing gases, a vacuum is drawn on the sterilizer chamber in which the container 60 is placed, step 340. More particularly, in step 340, the vacuum is drawn so the chamber is close to gas free as possible, a chamber pressure of 1 torr or less. This results in the evaluation of steps 274 and 276 placing the sensor module in the active state.

Once the vacuum is drawn, in a step 342, a measurement is made of the intensity of the light emitted by LED 180. Step 342 is executed by turning on LED 180 and the photodetector using the sub-steps described with regard to step 298. This initial measurement of detected light is referred to as $I_O$.

After the initial measurement of light intensity is made the sterilization process proceeds, step 344. Step 344 it is understood includes the introduction of the sterilant into the sterilization chamber.

Step 346 is the measurement of the gas to determine the concentration of the gas during the actual sterilization process. This process is a re-execution of the sub-steps performed in step 342 in order to determine the intensity of the light sensed by the photodetector. This measurement of light intensity is referred to as $I_A$.

Step 348 is the calculation of the concentration of gas measured in step 346. More particularly, in step 348 the processor using the Beers-Lambert law where C, the concentration of gas is determined according to the following formula:

$$C = -\ln(I_A/I_O)K \qquad (1)$$

where K is a constant.

As discussed above, in most sterilization processes it is anticipated that it is necessary to determine the concentration of one or more gases repeatedly over time period. To make these plural determinations of gas concentration, steps 346 and 348 are repeatedly executed. This is represented by the loop back from step 348 to step 346. Not shown are the process steps executed by the processor 242 to determine that it is no longer required to make the measurements needed to determine gas concentration. One variable that may be employed to make this determination is the elapsed time since the occurrence of some event during the sterilization process.

The method of determining gas concentration according to the method of FIG. 16 is not based on an absolute measurement of light intensity. Instead, this method is based on the relative difference between two measurements made during the same sterilization cycle. This method compensates for changes in the characteristics of the light emitted by the LED 180 and changes in the sensitivity of the photodetector 175. The method also compensates for changes in the physical structure of the components that reflect the light, mirror 196, and through which the light travels, window 190.

The same method may be used for determining the concentration of water vapor. In this execution of steps 342 and 346, the measurements of intensity of the light emitted by LED 170 are the measurements used to determine variables $I_O$ and $I_A$.

It is further feature of this version of the invention that each execution of step 346 to determine the intensity of the light when gas is present does not have to be immediately followed by the companion execution of step 348. In some versions of the invention, the plural measurements of light intensity $I_A$ obtained in the plural executions of step 346 are stored. Each one of these measurements may be stored with a time stamp indicating the time the measurement was made. After the sterilization cycle is completed, the processor 242, in the plural executions of step 348 uses the plural $I_A$ values and the single $I_O$ value to calculate the concentration of gas during the time period of interest.

By not executing step 348 after each execution of step 346 the sensor module does not have to be run in the fully active mode for the time needed to execute step 348. Here the fully active mode is understood to be the mode in which not only the processor 242 is fully operational but the components used to determine light concentration are also actuated. But not having to run in the fully active mode when performing the processing steps needed to determine gas concentrations the module draws less charge on the battery 230 than would be drawn if these determinations are made when the module 60 is in the fully active mode.

While not illustrated in FIG. 16 as part of executing step 342, the temperatures of the LED 170 or 180 is measured and recorded. The temperature of photodetector 175 is also measured and recorded. Each time a step 346 is executed the temperatures of the LED 170 and 180 and the photodetector 175 are also measured and recorded. As part of the process of generating the $I_A$ values the difference in LED and photodetector temperatures between when the $I_O$ and $I_A$ measurements are made are used to adjust for differences in the output of LED and the sensitivity of the photodetector.

IV. Alternative Means of Producing a Light Intensity Measurement that is Temperature Compensated In the first described method of determining light intensity of this invention, the output signal from the photodetector 175 is adjusted to compensate for variations in signal strength due to variations in temperature of the photodetector. The temperature signal from thermistor 177 is employed as a measure of the temperature when these calculations are performed.

Figure 17:
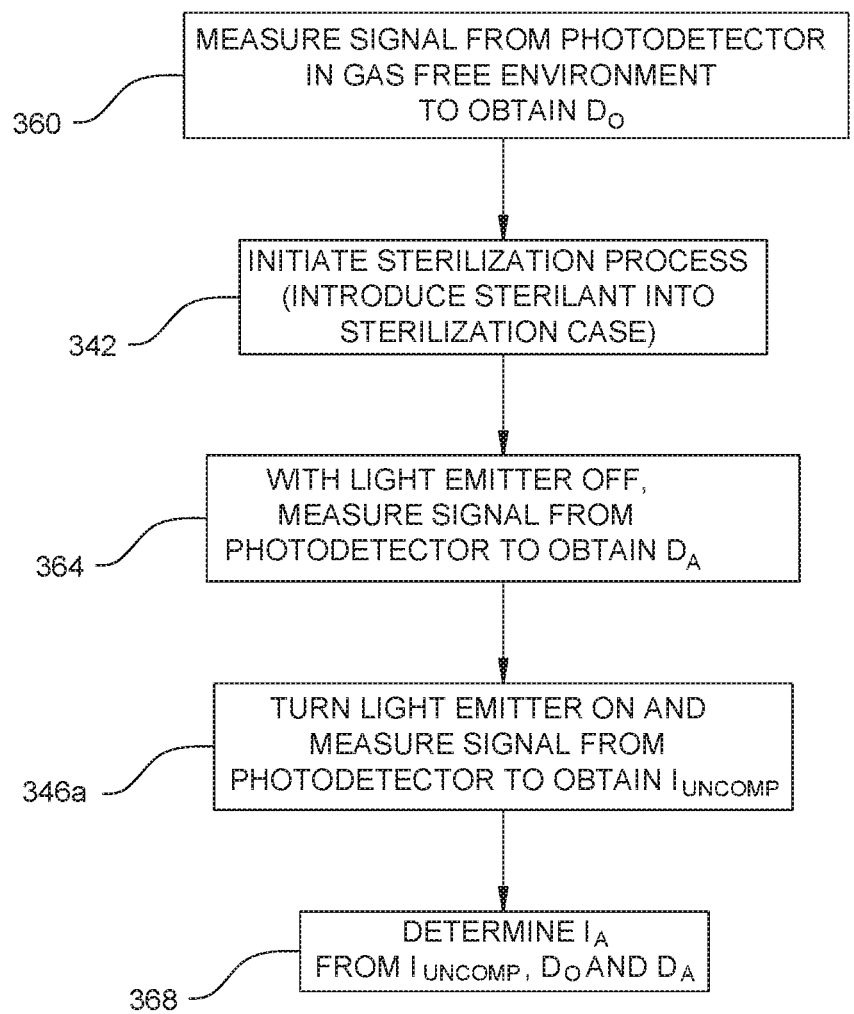
FIG. 17 is a flow chart of an alternative means of compensating for the effects of temperature on the signals produced by the photodetector of the sterilization container of this invention.

In an alternative version of the invention, variations in signal strength of the photodetector 175 may be compensated for without using a measure of photodetector temperature as an input variable. In this version of the invention, as represented by step 360 of FIG. 17, prior to the introduction of any sterilant into the container and prior to the actuation of LED 170 or LED 180 that emits light the concentration of which is measured, the signal output from the photodetector 175 is read. This signal is considered to have a strength $D_O$. The LED 170 or 180 is then actuated. If the process of FIG. 17 is combined with the process of FIG. 16, step 342 would be the next executed step. In other words, as a result of the actuation of the LED 170 or LED 180 the necessary $I_O$ measurement is obtained.

During the sterilization process it is still necessary to obtain the $I_A$ measurements of light intensity in order to determine gas concentration. Prior to making each one of these measurements, prior to each execution of step 346, a step 364 is executed. In step 364 the signal output by the photodetector without any light being shined directly on the photodetector is measured. This signal is considered to have strength of $D_A$. After the $D_A$ measurement is obtained, the LED 170 or 180 is actuated and the signal output by the photodetector 175 is considered to be the $I_{UNCOMP}$ measure of light intensity. Here the measure of intensity includes the subscript "uncomp" because this measurement that has not yet been compensated for temperature induced variations in the signal from the photodetector. Since this measurement of light intensity is essentially the same measurement that is made in step 346 it is identified as the execution of step 346*a* in FIG. 17. Then the processor, in a step 368, based on the above variables determines the $I_A$ the temperature compensated measurement of light intensity. Specifically, in step 368 the uncompensated measure of light intensity from photodetector 175 is converted into the temperature compensated measurement according to the following equation:

$$I_A = I_{UNCOMP} + (D_O - D_A) \quad (2)$$

This version of the invention eliminates the need to provide a temperature sensor adjacent the photodetector 175 in order to light intensity measurements that are compensated to account for temperature induced changes in the sensitivity of the photodetector.

It should be appreciated that step 360 could be performed immediately before or after step 342 of FIG. 16 is performed. Step 364 can likewise be performed immediately after step 346*a* is executed. Likewise there is no requirement that each execution of step 346*a* be immediately followed by the execution of the companion step 368. Thus, at the end of the sterilization process each of the $I_{UNCOMP}$ uncompensated measurements of light intensity may be converted into the $I_A$ temperature compensated versions of these measurements. The temperature compensated measurements are then, in the plural executions of step 348 be used to determine concentration of the gas of interest.

V. Alternative Versions of First Sensor Module

It should be understood that the sterilization container with sensor module of this invention may have features different from what has been described.

For example, alternative assemblies may be employed to measure the environmental characteristics that need to be measured in order to evaluate the effectiveness of the sterilization process. Thus, when it is necessary to measure the absorption of light at different wavelengths to measure the concentration of different gases, it may be desirable to provide plural photodetectors. Each one of the plural photodetectors is sensitive to a specific one of the wavelengths of the light the absorption of which is being measured. A benefit of this version of the invention is that, by making the plural measurements simultaneously, it is possible to determine for a given moment in time the concentrations of the plural gases of interest.

In still another version of the invention, the sensor assembly used to measure the concentrations of plural gases may include a single light source and/or a single light sensitive transducer. More specifically, the light source may emit light over a range of wavelengths. This range of wavelengths it is understood includes the wavelengths of light that are absorbed by the gases for which the concentration measurements are required. Thus, the light source could emit white light, light over the full range of the wavelengths of visible light.

The single transducer could be a spectrometer or an FTIR. The output from the spectrometer or FTIR is a measure of light intensity over a range of frequencies. Based on a measurement, the processor 242 determines the intensity of light for the frequencies of interest. This version of the invention can, like the version of the invention with plural photodetectors, can be used to determine, at a given moment in time, the concentrations of the plural gases of interest.

Likewise there is no requirement that in, all versions of the invention, the light the absorption of which being measured be reflected or when reflected be reflected on a single back-and-forth path. In some versions of the invention, the light emitter (emitters) and complementary detector (detectors) may be spaced apart from each other. The light may travel along a single line path from the emitter to the detector. In this version of the invention, the sensor module is not provided with an assembly for reflecting the light.

As depicted in FIG. 18, the module may be constructed so that the light as it travels between the emitter 380 and detector 388 is reflected a number of times. In FIG. 18 installed in the sensor module are two parallel mirrors 384 and 386. Mirror 384 is depicted as longer than mirror 386. The light beam 382 emitted by emitter 380 strikes mirror 384 and then strikes mirror 386. The light then is repeatedly reflected back and forth between mirrors 384 and 386. After reflecting off mirror 384 one last time the light strikes the detector 388.

In this version of the invention the path of travel of the light is greater than the distance along the length of the mirrors 384 and 386. This makes it possible to, in a given volume have the light travel along a path that is greater than the length of the major axis through the volume. This is advantageous because the longer the path of the light through the volume in which the gas is present, the more light will be absorbed by the gas. This makes it possible to, based on a measure the absorbed gas, provide a measure of gas concentration.

As depicted in FIG. 19, in still another version of the invention a beam of light 402 emitted by an emitter is applied to a collimator 404. The collimator narrows the light beam. The reflector 406 that reflects the light to detector 388 is a prism like assembly with plural reflective surfaces. The light beam is reflected onto one of the surfaces, continues to transit through the reflector 406 before being reflected off a second surface and out of the reflector. The light beam 402 passes through a filter 408 before striking the detector 388. A benefit of providing these components internal to the sensor module is that the light beam 402 that strikes the detector 388 should consist of photons that are both focused on the detector and essentially all at the wavelength the measurement of which is use for determining gas concentration.

In still other versions of the invention, the path along which the beam of light the intensity of which is measured is bent or curved with the use of concave mirrors or fiber optic cables.

If appropriate, the sensor module of the sterilization container of this invention may be provided with plural collimators 404 of filters 408. In versions of the invention wherein the light emitter is a coherent light source, a laser, it be possible to eliminate these components.

Likewise, it should be understood that in other versions of the sterilization case of this invention sensors other than light intensity sensors may be used to monitor gas concentration. For example, passive components the characteristics of which vary as function of gas concentration may be employed as these transducers. Thus, it is within the scope of this invention that resistors or capacitors the characteristics of which change as a function of gas concentration be employed as the sensors of this invention.

Similarly there is no requirement that in all versions of the invention the sensor module be mounted to the container lid. In alternative versions of the invention, the sensor module is mounted to the bottom, front, rear or one of side panels of the case of the container.

The number and type of sensors are understood to be a function of the potential sterilization processes to which the sterilization container can be subjected. For example, if ethylene oxide is one of the sterilizing gases to which container could be exposed, then the sensing module includes sensing components that provide signals representative of the concentration of this gas. Some versions of the invention may have plural sensors for monitoring the temperature within the container. These plural sensors are typically located so that at least one sensor is positioned in a space in which there is relatively unimpeded gas flow. The second sensor is located within a space in which structural features impede the flow of gas around the sensor. Alternatively, in terms of gravity, the sensors are spaced apart from each other so that one sensor is located above the other sensor. The signals representative of container temperature output by these signals are used by the processor to determine whether or not the container is saturated with steam.

Not all versions of the invention may have all of the above described components. For example, it may not be necessary to provide the heating elements adjacent the windows through which the light emitted as part of the gas measurement process or the mirrors that reflect this light.

In some versions of the invention, it may be possible to provide the emitter/emitters that emit light for the gas/vapor measurement process and the complementary detectors in the same sealed housing. These versions of the invention may not include any mirrors for reflecting light.

Alternative means may be provided for outputting the data and information generated by the sensor. For example, it is within the scope of this invention to provide the sensor module with a transmitter. Typically this transmitter is wireless. In versions of the invention in which the transmitter is an RF transmitter, the transmitter is also able to receive signals. In this version of the invention, processor 242 may perform evaluations to determine whether or not the sterilization process as a whole or a particular phase (step) has been completed. If this evaluation tests true, the processor causes the transmitter to transmit this information to a complementary receiver integral with the sterilizer. The sterilizer, upon receipt of this information advances to the next step of the sterilization process or presents this information on a display.

In some versions of the invention, the module components that present information regarding the sterilization state of the instruments in the module may only be pulse on. This again is to minimize the drain of charge on the battery.

Some sterilization containers of this invention may include one or more valves. These valves open and close inlet ports into the container with which the valves are integral. In these versions of the invention, the processor, based on whether measurements indicating whether or not the container is being subjected to a sterilization process, asserts the command signals that open and close these valves. Similarly, there is no requirement that in all versions of the invention the sensor module be mounted to the lid. In alternative versions of the invention the module may be mounted to one of the panels that form the container body.

Likewise, while it is believed preferred that sensor and other components of the sensor module be located inside the container, it is within the scope of this invention that anywhere from one to all of the components of the sensor module be mounted to the container to be located outside of the container. In these versions of the invention, typically at least some if not all of the sensors will be disposed inside the container. Some of these versions of the invention will includes components that facilitate the communication of the signals from the sensors inside the container to the components located outside of the container.

Alternative constructions of the physical features of the invention may also vary from what has been described. For example, the temperature sensitive transducers 172, 177 and 182 may be mounted directly to the photodetectors or LEDs the temperatures of which the transducers monitor.

Likewise it may be desirable to adjust the levels of the currents applied to the light emitters 170 and 180. This adjustment would compensate for changes in the ability of the light emitters to emit substantially the same quantity of light over the life time of the emitters. This helps maintain the $I_O$ values of light substantially constant.

VI. Sterilization Container with Sensor Module Suited to Detect Steam State

FIGS. 20 and 21 depicted a portion of an alternative sterilization container of this invention. This sterilization container includes a sensor module 444. The sensor module 444 is attached to one of the panels 442 of a sterilization container. Sensor module 444 includes a shell 446 that functions as the outer body of the module. The shell 446 is generally rectangularly shaped. Shell 446, like the other components of this invention exposed to sterilant, is formed from a material able to withstand the corrosive effects of the sterilant.

Feet 448 (two identified) project outwardly from one of the major outer surfaces of shell 446. Feet 448 are the elements of the module 444 that abut the panel 442 to which the module is attached. Feet 448 are made from material that has relatively low thermal conductivity, typically at or less than 0.5 Watts/m-° K. Feet 448 are formed from material of low thermal conductive to minimize the extent to which there is an exchange of thermal energy between sterilization container 440 and sensor module 444.

Shell 446 is formed to define three internal voids. A primary void, void 452, in terms of surface area is the largest of the three voids. There are two additional voids 454 and 464 located immediately inward of one of the outer walls of the shell. A web 453 internal to the shell separates void 452 from voids 454 and 464. Voids 454 and 464 are open to the environment in the sterilization container 440 through an opening 456 in the shell. The space in the shell above the opening 456 is considered to be void 454. The space below opening 456, void 464. A T-shaped flow diverter 458 is located internal to the shell 446 immediately inward of opening 456. Diverter 458 is the mechanical component of sensor module 444 that separates void 454 from void 464.

Four bores are formed in web 453. Two of the bores, bores 466, (one identified) are located on opposed sides of opening 456 and diverter 458 and are relatively close to the diverter. One bore 466 extends from void 452 to void 454. The second bore 466 extends from void 452 to void 464. The remaining two bores, bores 468, (one identified) are also located on opposed sides of opening 456 and diverter 458. Bores 468 are spaced distal to the diverter 458. One bore 468 extends from void 452 to void 454. The second bore 468 extends from void 452 to void 464.

Module 444 is further formed to have an outlet port 470. The outlet port 470 is formed in the outer wall of the shell so as to open from the lowest portion of void 454. A valve 472 is mounted to the module 444 so as to extend over the outlet port 470. Valve 472 normally closes the portal between outlet port 470 and the adjacent environment internal to the container 440. When valve 472 is closed, gaseous state fluid is not able to pass through port 470. Thus, it should be appreciated the sensor module is designed so that gas cannot normally flow between the space within the sterilization container and the base of void 464. The valve 472 is set to open when liquid is in the base of void 464. In the depicted version of the invention, the valve 472 is a float valve. In other words in the absence of valve 472 being open, void 464 is a closed end void.

A pressure sensor 476 (one identified) is mounted in each of the bores 466. A temperature sensor 478, shown symbolically, is disposed in void 452. Temperature sensor 478 sources a signal representative of the temperature at or near the pressure sensors 476. In some versions of the invention, integral with each pressure sensor 476 is a temperature sensor 478 that provides an indication of temperature of the pressure sensor 476.

A temperature sensor 480 (one identified) is disposed in each of the bores 468. Given that bores 468 are spaced away from opening 456 it should be understood that one temperature sensors 480 is spaced above opening 456 and located in void space 454. The second temperature sensor is located below the opening 456 so as to be located in void space 464. The second temperature sensor 480 is further understood to be located above the base of void space 464. Each temperature sensor 480 includes a closed end sleeve 482 in which the actual temperature sensitive transducer is seated. (Transducer not illustrated.) The sleeves 482 are positioned to be spaced away from the walls that define the perimeters of the void 454 and 464 into which the sleeves protrude.

It is understood that sensors 476 and 480 are mounted to web 453 in such a manner that fluids, including pressurized steam, cannot enter void 452. This substantially eliminates the likelihood that gases and vapors that surround the shell and enter voids 454 and 464 can adversely affect the components disposed in void 452.

The components that monitor the signals output be sensors 476 and 480 and that evaluate the measurements made by the sensors are disposed in void 452. As the structures of these components are not part of the present invention, they are not illustrated. It should be understood that these components include a processor similar to previously described processor 242. The temperature measurements made by the one or more temperature sensors 478 are employed by the processor to generate pressure measurements that are compensated to adjust for changes in the temperature of the pressure sensors 476.

Also disposed in void 452 are cells 484. Cells 484 supply the charges required to energize both the sensor 476 and the components internal to the module that store and evaluate the signals representative of the container environment.

A sterilization container 440 that includes sensor module 444 is used in a manner identical to how a conventional sterilization container is used. During a sterilization process, sterilant enters voids 454 and 464 through opening 456. Some sterilization processes include at least one step in which the instruments being sterilized must be in a saturated steam environment.

To determine whether or not instruments are in a saturated steam environment, the processor internal to the module 444 first reads the pressure as measured by one of the pressure sensors 476 and the temperature as indicated by the upper of the two temperature sensors 480. By reference to steam data tables, these data indicate the state of the steam in void 454. These data may indicate that steam is present in void 454. However, this data does not indicate if the steam is in the same state throughout the whole of the container.

To make this determination, the processor evaluates whether or not the environmental temperatures as measured by both temperature sensors 480 are substantially equal and near a target temperature. This target temperature is the temperature of saturated steam at a given absolute pressure. Generally, this target temperature is near 132° C. As a result of this evaluation it may be determined that the temperature of void 464 is less than the temperature of void 454. When the gases in the sensor module 444 are in this state, there is high likelihood that the gas in void 464 includes a sizeable fraction of air. This means closed ended voids defined by the instruments in the container may still contain a sizeable fraction of air. Accordingly, should the processor determine that the temperatures in voids 454 and 464 are in this state, the processor considers the environment in the container to be one in which the instruments are not essentially surrounded by saturated steam.

Alternatively, the evaluation may indicate that the gases in voids 454 and 464 are essentially equal and near the target temperature. When the gases are in this state void 464 is essentially entirely filed with vaporized water vapor (saturated steam). Accordingly, the sensor module processor interprets this result as indicating that the instruments in the sterilization container are essentially completely surrounded by saturated steam.

There may be times the steam in the void 464 condenses. When this event occurs, the now liquid state water flows towards outlet port 470. The liquid-state water valve causes the valve 472 to open. The liquid state water thus flows out of the void space 464. This prevents the pooling of water in the sensor module.

It should be understood that sensor module 444 is often mounted immediately above the bottom panel of the container body 62. For example less than 3 cm above the bottom panel and often 2 cm or less above this panel. This is because owing to water vapor being less dense than air, it is bottom of the container body 62 that is the last portion of the container to fill with saturated steam. By placing module 44 adjacent the bottom of the container, the signals from the module provide measurement upon which it can be determined whether or not this portion of the container has filled with steam.

VII. First Alternative Sensor Module Suited to Detect Steam State

Figure 22:
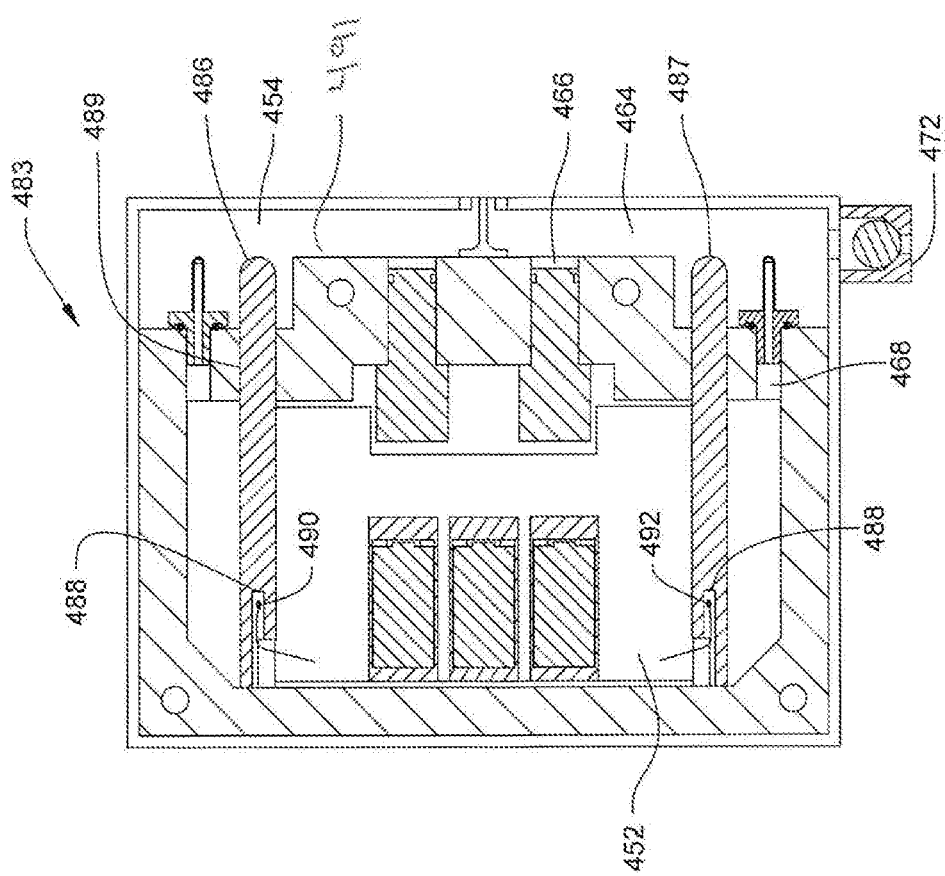
FIG. 22 is view depicting the interior of a first alternative version of the sensor module of FIG. 21.

An alternative sensor module 483 that can be mounted to a panel 442 (FIG. 20) of a sterilization container is now described by reference to FIG. 22. Sensor module 483 includes many of the same components of sensor module 444. To reduce redundancy, these components will not be re-described unless necessary.

Sensor module 483 includes a web 491 that is substitute for web 453 of sensor module 444. Web 491 includes the previously described bores 466 and 468, one of each identified. Web 491 is formed with two additional bores, bores 489 one identified. A first one of the bores 489, extends between void 452 and void 454. The second bore 489 extends between void 452 and void 464.

An elongated, rod-like thermal mass is disposed in each bore 484. A first thermal mass, mass 486, protrudes into the void 454 associated with the bore 489 that opens into void 454. The second thermal mass, mass 487, protrudes into void 464 associated with the bore 489 that opens into void 464. The opposed ends of both thermal masses 486 and 487 extends into void 452. The thermal masses 486 and 487 are both formed from material that has a relatively high specific heat per unit volume. One definition of specific heat per unit volume for thermal masses 486 is that they have a higher specific heat per unit volume than the specific heat per unit volume of the surrounding structural features of the sensor module 483. Thus if web 491 is formed from aluminum, thermals masses 486 and 487 may be formed from stainless steel. While not illustrated, in some versions of the invention each thermal mass 486 and 487 is encased in a tube like insulating sleeve. The sleeve extends between the inner surface of the web 491 that defines the bore 484 in which the thermal mass is seated and the mass. The sleeves are formed from material that is less thermally conductive than either the web 491 or the thermal masses 486 and 487.

In the depicted version of the invention, each thermal mass 486 and 487 is formed to have a closed end bore 488. The bore 488 extends inwardly from the end of the mass 486 or 487 seated in void 452. A temperature sensor is mounted in each bore 488. In FIG. 22, temperature sensor 490 is seated in the thermal mass 486. Temperature sensor 492 is seated in the thermal mass 487.

Sensor module 483 is used to determine state of the steam in the sterilization container in which the module is mounted. Sensor module 483, like sensor module 444, is mounted to one of the vertically oriented panels of the container body 62 so that by reference to gravity void 454 is above void 464.

The sensor module 483 operates based on the principle that saturated steam is more thermally conductive than either condensate, (liquid state water) or superheated steam at the same temperature and pressure. Superheated steam it is understood, is steam that is at a temperature greater than the vaporization pressure at the absolute pressure at which the temperature is measured. When the sterilization container starts to fill with steam, void 454, being above void 464 fills with the seam prior to void 464 filling with steam. During this time period, time period A in FIG. 23, owing to the saturated steam in the upper void 454 having a higher thermal conductivity than unsaturated or superheated steam in lower void 464, the transfer of thermal energy into the topmost thermal mass 486 results in the temperature of this mass increasing at a relatively high rate, mathematically, $dT_U/dt$ where $dT_U$ is the change of temperature of mass 486 as measured by sensor 490 per unit of time dt. During time period A the air and unsaturated steam in lower located void 464 is less thermally conductive. Accordingly, during time period A, $dT_L/dt$ is less than $dT_U/dt$. Here $T_L$ is the temperature of mass 487 as measured by sensor 492. In FIG. 23 this is graphically depicted by during time period A the slope of the temperature change of mass 486, represented by solid line 502, is greater than the slope of the temperature change of mass 487, represented by dashed line 504.

Eventually the whole of the sterilization container fills with steam. This means that both module voids 454 and 464 are filed with saturated steam. When the sterilization container is in this state, the rate of heat transfer from the steam in void 454 to thermal mass 486 and from the steam in void 464 to thermal mass 487 should be substantially identical. During this time period, time period B in FIG. 23, $dT_L/dt$ should therefore substantially equal $dT_U/dt$.

Accordingly, in this version of the invention, the processor, that receives the signals from temperature sensors 490 and 492 continually uses these signals to determine the temperatures of the upper thermal mass 486 and the lower thermal mass 487. The processor uses these signals to determine $dT_U/dt$ for upper void 454 and $dT_L/dt$ for lower void 464. The processor compares the rates of $dT_U/dt$ and $dT_L/dt$ for the same time periods. Based on this comparison, the processor determines whether or not the serialization container to which sensor module 444 is mounted can be considered essentially filed with saturated steam. The results of this evaluation is used as one of the inputs to determine whether or not the articles in the containers have been subjected to a validated sterilization process.

There may be a possibility that the steam in the sterilization containers enters superheated state. As mentioned above, the thermal transfer properties of superheated steam less than that of saturated steam. The processor uses the signals from the pressure sensors 466 to determine the vaporization (boiling) point of the water vapor based on these pressure measurements. The temperature measurements from sensors 480 can be used to determine if the steam is at a temperature of the boiling point. If this evaluation tests true, the processor can use this result as indication that the sterilization container, as opposed to be filled with saturated steam, is filled with superheated steam. The fact that the sterilization container may be in this state can be used as another input variable to determine whether or not the article in the container have been subjected a validated sterilization process.

Variations of this evaluation of steam state are possible. Most significantly, even in a saturated steam environment, dT/dt is a function of the current temperature. The temperature of the bottom thermal mass 487 may be less than that of the upper thermal mass 486 even when both masses are surrounded by saturated steam. This means during these time periods $dT_U/dt$ and $dT_L/dt$ may not be equal even though both masses are surrounded by saturated steam. To compensate for this fact, the processor may not compare the simultaneous values for these rates. Instead, the processor may compare these rates when the masses 486 and 487 are at the same temperature. Again, before the conditions in the sterilization container stabilize, the temperature of the lower thermal mass 487 is often below that upper thermal mass 487. This means that the processor does not perform the $dT_U/dt$ to $dT_L/dt$ comparison until after lower thermal mass 487 reaches a temperature that was previously reached by the upper thermal mass 486.

In some versions of this module, the exposed surfaces of the thermal masses may not be disposed within void spaces of the sensor module. Instead the thermal masses may simply form exposed faces of the sensor module. Thus, in some versions of the exposed faces of the thermal masses may even be flush with or recessed relative to the adjacent surfaces of the sensor module.

In some versions of the invention may also be necessary to compare one or both of $dT_U/dt$ or $dT_L/dt$ to calibrated temperature rates of change to determine whether or not the articles in the sterilization container were properly sterilized.

VIII. Second Alternative Sensor Module Suited to Detect Steam State

A second alternative sensor module 520 able to module steam state for incorporation into a sterilization container of this invention is now described by reference to FIG. 24. Module 520 is based on module 444. To reduce redundancy components common to both modules 444 and 520 where possible are not described again.

One difference between modules 444 and 520 is that module 520 does not include a diverter. Thus in this version of the invention, web 453 separates void 452 from a single void 522. Opening 456 opens into void 522. Further in this version of the invention, valve 472 is spaced away from the section of void 522 that extends top-to-bottom along the length of the module 520.

Two transducers are mounted in module 520 so as to be located at opposed ends of void 522. A first transducer, transducer 526 is mounted in side module 520 so as to be located a top end of void 522. Transducer 526 emits a signal either the sonic or ultrasonic wavelengths. The second transducer, transducer 528, is mounted inside module adjacent the bottom end of void 522. Transducer 528 is positioned so that the energy emitted by transducer 526 will strike transducer 528. Transducer 528 is a receiver that generates a variable signal as a function of the amount of energy emitted by transducer 526 that strikes transducer 526.

This version of the invention is also used to determine the extent to which the sterilization container to which module 520 is attached is filled with saturated steam. To use module 520, the time between when the sonic or ultrasonic energy emitted by transducer 526 and received by transducer 528 is measured. This signal is measured because the speed of sound is greater in volume filled with saturated steam in comparison to the same volume filled with less than saturated steam or superheated steam. This difference in the speeds sound means that the sound will travel faster through void 522 when the void is filled with steam in this state. The times of flight of these energy emissions are compared to a table of stored references times for these signals. Based on these comparisons the processor determines the extent to which the sterilization container is filled with 100% saturated steam.

In versions of the invention in which the sensor module is provided with two thermal masses 486 and 487 it is likewise only necessary that one of the thermal masses be contained in the closed end void space. In these versions of the invention, the thermal mass 486 not in the closed end void space can be located at or below the thermal mass 487 in the void space. In some versions of the invention the sensor module may only contain a single thermal mass. This would be the thermal mass the exposed end of which is the closed end void space.

IX. Alternative Versions of Second Sensor Module

Alternative versions of module 444, 483 and 520 are possible. For example, the readings from the plural pressure sensors 476 should be identical. Therefore, one of the pressure sensors 476 can be omitted. When plural pressure sensors are provided, one sensor can serve as a check on the other sensor or be present as a back-up sensor.

Likewise, there is no requirement that in these versions of the invention both temperature sensors 480 be located in the enclosed void space. For the signals from the sensors to be used to evaluate the state of steam, at least one of the sensors needs to be located in the enclosed void space so as to be located below the opening into the void space. This is because if the contents of the sterilization container are filled with less than saturated steam, the void space will most likely be at least partially filled with gas other than saturated steam. This means that when the temperature inside the void space is compared to the temperature of the surrounding environment, the temperature in the void space will be less than that of the surrounding environment. If the sterilization container is filled with saturated steam, than the steam will have forced the other gases out of the void space and substantially have filled the void space. The temperature of the void space as measured by the sensor in the void space should be substantially equal to the reference temperature measured by the second sensor. Here, "reference temperature" is understood to be the temperature in the upper located void space or the temperature of the unenclosed environment inside the container as measured by the second sensor.

This means that it us within the scope of this invention to construct a module wherein the sensor contained in the enclosed void space is, relatively to gravity, at the same height or even located above the temperature sensor located within the unenclosed environment inside the container.

An advantage of enclosing both sensors is that the structural components forming the sensors, the sleeves 482, tend to be fragile. Enclosing both temperature sensors 480 reduces the likelihood that unintended contact with the sensors can result in their breakage.

In versions of the invention wherein the plural temperature sensors are enclosed in the void space, there may be plural openings into the void space. Generally though the temperature sensor 480 located in the enclosed void space is, relative to gravity, located below the opening into the void space.

It is further within the scope of this invention that three or more sensors be provided to measure container temperature in order to determine steam state. Thus with a three temperature sensor 480 version of this invention, two of the sensors may be located at different heights within the enclosed void space. These sensors would then provide an indication when the sterilization container is first partially filled and then, secondly, substantially filled with saturated steam.

In some versions of the invention the valve the allows the flow of liquid out of the closed end void space may be emitted. A screw may substitute for this valve. Alternatively, if the sensor module is removably mounted to the sterilization container, condensate can be cleaned out of the void space during the process of cleaning the module.

X. Alternative Embodiments

The above are directed to specific versions and embodiments of this invention. The invention may have features different from what has been described.

Thus, the features of the different versions of the invention can be combined. For example, the feature of normally having the sensor module in the sleep state, periodically transitioning to a peek state and, when appropriate, transitioning to an active state, can be incorporated into each of the sensor module of this invention. Likewise the feature of, when in the active state, only periodically measuring the characteristics of the environment inside or adjacent the sterilization container may be incorporated into each sensor module of this invention.

Similarly, there is no requirement that all the features of each described version of the invention be incorporated a particular version of the invention. For example, in the versions of the invention wherein thermal masses 486 and 487 and temperature sensors 490 and 492 attached to these masses are mounted to the sensor module to determine the presence of saturated steam, it may not be necessary to provide the module with additional temperature sensors.

Likewise the sterilization containers of this invention may have features different than what has been described. For example, the vent holes and filter assembly may be mounted to the body of the container instead of the lid. In some versions of the invention both the body container and the lid are provided with vent holes and filter assemblies.

It should likewise be understood that the structure of the sensors integral with the modules of this invention may vary from what has been described. Thus, it is within the scope of this invention that a single pressure sensor provide the signals representative of container pressure for the whole range of pressure for which this measurement is needed. It is within the scope of this invention, that if there are plural pressure sensors that each pressure sensor be contained in its own chamber. In some sub-species of this version of the invention, a single sensor frame or shell may be shaped to define these individual chambers.

In still other versions of the invention, the transducer employed to generate signals representative of container temperature may not be a thermistor. In alternative versions of the invention, one or more thermocouples may perform this function. Thus, it is within the scope of this invention that a first transducer provides a measure of temperature over a first range of temperatures and a second transducer provides a signal representative of temperature over a second range of temperatures.

In versions of the invention in which a component integral with the sensor module provides information regarding the effectiveness of the sterilization process, this component may not always be a selectively actuated light. The component may be a RF transmitter. In these versions of the invention, a low powered receiver is also integral with the sensor module. In response to an interrogation signal received by the receiver, the transmitter outputs data from the processor 242 regarding the effectiveness of the sterilization process. In these versions of the invention, the window through the container body or lid through the RF energy is transmitted may not be transparent to light. Instead, this window is formed of material that does not absorb the transmitted RF energy to a level at which it cannot be effectively processed by the components both internal to and external from the container.

Likewise there is no requirement that in all versions of the invention the sensor modules be mounted inside the containers with which the modules are integral. In some versions of the invention the sensor modules are mounted to an outer surface of the container base or lid. Ports in the structural member to which the module 80, 444, 483 or 520 is mounted expose the sensor module sensors to the environment internal to the container. Some if not all of the sensors may be disposed inside the container.

There is no requirement that in all versions of the invention the processor that, based on the sensor signals, evaluates the sterilization process be located in the sensor module 80, 444, 483 or 520. In some versions of the invention, the sensor module may include components that transmit the container environmental measurements to a processor integral with the sterilizer. The sterilizer processor performs the evaluation regarding whether or not the measured environmental characteristics indicate that the contents of the sterilization container were properly sterilized. Alternatively, based on the measurements of the environmental characteristics received from the sensor module 80, 444, 483 or 520, the sterilization processor makes real time adjustments to the sterilization process being executed. These adjustments, for example include lengthening the time the container is exposed to sterilant to ensure the components 64 in the container are properly sterilized. It is further within the scope of this invention that the external processor to which the sensor module transmits the data describing the measured environmental characteristics be a process separate from the processor integral with the sterilizer.

It is thus an object of the appended claims to cover all such variations and modifications that come within the true spirit and scope of the invention.

What is claimed is:

1. A sterilization container assembly for sterilizing a surgical instrument, said sterilization container assembly comprising:
    a container defining an interior shaped to hold the surgical instrument and adapted to allow steam to enter said container to sterilize the surgical instrument;
    a sensor module disposed within said interior of said container, said sensor module is shaped to define a closed end void space and at least one opening that forms a fluid communications path from the interior of the container into said closed end void space;
    said sensor module comprising:
        a pressure sensor for sensing a pressure inside said container;
        a first temperature sensor for sensing a temperature inside said container;
        a first thermal mass, the first thermal mass having a first end disposed in said closed end void space and a second end spaced from the first end so as to not be located in said closed end void space; and
        a second temperature sensor is mounted to said sensor module so as to monitor a temperature of the second end of the first thermal mass.

2. The sterilization container assembly of claim 1, wherein the sensor module is further constructed so that:
a structural member that partially defines said closed end void space;
said first thermal mass is mounted to said structural member so that the first end of the first thermal mass is exposed to said close end void space; and
wherein said structural member further defines an enclosure enclosing said second end of said first thermal mass.

3. The sterilization container assembly of claim 1, wherein the sensor module is further constructed so the first end of said first thermal mass projects into said closed end void space.

4. The sterilization container assembly of claim 1, wherein said sensor module further includes a valve mounted to the sensor module adjacent said closed end void space, said valve being adapted to block gas flow through the valve and allow condensate to flow out of said closed end void space.

5. The sterilization container assembly of claim 1, further comprising a second thermal mass having a first end disposed in said closed end void space that, relative to gravity, is located above the first end of said first thermal mass and a second end spaced from the first end of the second thermal mass so as to not be located in said closed end void space; and
a third temperature sensor is mounted to the second end of said second thermal mass so as to sense a temperature of said closed end void space by sensing a temperature of said second thermal mass.

6. The sterilization container assembly of claim 5, wherein the sensor module is further constructed so that said first end of each of the first thermal mass and said second thermal mass are contained in an undivided closed end void space.

7. The sterilization container assembly of claim 1, wherein said second temperature sensor is mounted to the second end of said first thermal mass so as to determine a change in temperature of the first thermal mass per unit of time by sensing the temperature of said first thermal mass during a defined time period.

8. A sterilization container for placement within a sterilizer, said sterilization container comprising:
a body defining an interior shaped to hold surgical instruments and adapted to allow steam to enter said body in order to sterilize the surgical instruments;
a sensor module defining a void space, said void space of said sensor module in fluid communication with said interior of said body;
a first thermal mass having a first end disposed in said void space and a second end spaced from said first end so as to not be located in said void space; and
a first temperature sensor mounted to said first thermal mass so as to monitor a temperature of said second end of said first thermal mass.

9. The sterilization container of claim 8, wherein said sensor module further comprises:
an opening defining fluid communication pathway between said void space of said sensor module and said interior of said body; and
a sealed enclosure defining an enclosed void space separated from said void space, said sealed enclosure configured to prevent fluid communication between said void space and said enclosed void space;
wherein said first end of said first thermal mass is positioned within said void space, relative to gravity, below said opening; and
wherein said second end of said first thermal mass is disposed in said enclosed void space.

10. The sterilization container of claim 9, wherein said first temperature sensor is mounted to the second end of said first thermal mass so as to determine a change in temperature of the first thermal mass per unit of time by sensing the temperature of said first thermal mass during a defined time period.

11. The sterilization container of claim 9, further comprising:
a second thermal mass having a first end disposed in said void space that, relative to gravity, is located above the first end of said first thermal mass and a second end spaced from the first end of the second thermal mass so as to not be located in the void space; and
a second temperature sensor is mounted to the second end of said second thermal mass so as to sense a temperature of the second end of said second thermal mass.

12. The sterilization container of claim 11, wherein said sensor module is constructed so that said first end of said first thermal mass and said first end of said second thermal mass are contained in an undivided space within said void space.

13. The sterilization container of claim 11, wherein said sensor module is constructed so that a single opening provides a fluid communication path from said interior of said body into the void space; and
a flow diverter is mounted to said sensor module inward of said single opening to separate said void space into a first void space and a second void space such that said first end of said of said first thermal mass is disposed in said first void space and said first end of said second thermal mass is disposed in said second void space.

14. The sterilization container of claim 9, wherein said first thermal mass is encased in an insulating sleeve formed from material that is less thermally conductive than either of said sealed enclosure or said first thermal mass; and
wherein said insulating sleeve extends between an inner surface of said sealed enclosure that defines a bore in which said first thermal mass is seated and an outer surface of said first thermal mass.

15. The sterilization container of claim 8, further comprising: a second opening in said void space below said opening; and
a valve coupled to said second opening in said void space, said valve being adapted to prevent gas from entering said void space via said second opening and to allow condensate to exit said void space.

16. A method of sterilizing at least one surgical instrument, said method including the steps of:
placing at least one surgical instrument in an interior of a sterilization container, the sterilization container being formed to allow steam to enter the interior of the sterilization container, the sterilization container including:
a first temperature sensor configured to measure a temperature in the interior of the sterilization container;
a first thermal mass having a first end opposite a second end;
a second temperature sensor mounted to said first thermal mass and configured to measure a temperature of the second end; and a sensor module having a void space and an opening from the interior of the sterilization container into the void space, at least a section of the void space being, relative to gravity, located below the opening, wherein the first thermal mass is mounted to the sensor module so first end protrudes into the void space; introducing steam into the interior of the sterilization container;

measuring the temperature in the interior of the sterilization container;

measuring the temperature of the first thermal mass;

comparing the temperature measured by the second temperature sensor to the temperature measured by the first temperature sensor; and based on the temperature measurements and the comparison of the temperature measurements, determining an extent to which the sterilization container is filled with saturated steam.

17. The method of claim 16, further comprising the step of comparing the temperature measured by the first temperature sensor to a temperature measured by a third temperature sensor that is mounted to and configured to measure the temperature of a second thermal mass (486), the second thermal mass having a first end at least partially disposed in the void space at a location, relative to gravity, that is above the first end of said first thermal mass.

18. The method of claim 17, further comprising continuously introducing steam into the interior of the sterilization container until the temperature measured by the first temperature sensor is the same as the temperature measured by the third temperature sensor indicating the extent to which the sterilization container is filled with saturated steam.

19. The method of claim 16, wherein the sterilization container includes at least one pressure sensor capable of monitoring a pressure in the interior of the sterilization container, the method further comprising:

during said step of measuring the temperature in the interior of the sterilization container and said step of measuring the temperature in said section of the void space, with the at least one pressure sensor, measuring the pressure in the interior of the sterilization container; and in said step of determining the extent to which the sterilization container is filled with saturated steam, making the determination based on the pressure in the interior of the sterilization container as measured by the at least one pressure sensor.

\* \* \* \* \*